(12) United States Patent
Wagner et al.

(10) Patent No.: US 12,703,735 B2
(45) Date of Patent: Aug. 11, 2026

(54) METHODS AND COMPOSITIONS FOR ENGINEERING CD4-DEFICIENT CAR T CELLS AND ANTI-CD4 CAR T CELLS AND USES THEREOF

(71) Applicant: Seattle Children's Hospital, Seattle, WA (US)

(72) Inventors: Thor Wagner, Seattle, WA (US); Jaya Sahni, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 1144 days.

(21) Appl. No.: 17/435,535

(22) PCT Filed: Mar. 17, 2020

(86) PCT No.: PCT/US2020/023117
§ 371 (c)(1),
(2) Date: Sep. 1, 2021

(87) PCT Pub. No.: WO2020/190925
PCT Pub. Date: Sep. 24, 2020

(65) Prior Publication Data

US 2022/0054549 A1 Feb. 24, 2022

Related U.S. Application Data

(60) Provisional application No. 62/820,387, filed on Mar. 19, 2019.

(51) Int. Cl.
*C07K 14/73* (2006.01)
*A61K 40/11* (2025.01)
(Continued)

(52) U.S. Cl.
CPC ........ *C07K 14/70514* (2013.01); *A61K 40/11* (2025.01); *A61K 40/31* (2025.01);
(Continued)

(58) Field of Classification Search
CPC .......... C07K 14/70514; C07K 2317/21; C07K 16/2803; C07K 14/7051; C07K 2317/622;
(Continued)

(56) References Cited

U.S. PATENT DOCUMENTS 9,951,118 B2 4/2018 Kitchen et al.
10,273,280 B2 4/2019 Ma et al.
(Continued)

FOREIGN PATENT DOCUMENTS

WO WO 16/138491 9/2016
WO WO-2016138491 A1 * 9/2016 ............. A61K 35/15
(Continued)

OTHER PUBLICATIONS

Kleiveland CR. Peripheral Blood Mononuclear Cells. In: Verhoeckx K, Cotter P, López-Expósito I, et al., editors. The Impact of Food Bioactives on Health: in vitro and ex vivo models [Internet]. Cham (CH): Springer; 2015. Chapter 15 (Year: 2015).*
(Continued)

*Primary Examiner* — Tracy Vivlemore
*Assistant Examiner* — Thomas R. Amick
(74) *Attorney, Agent, or Firm* — KNOBBE, MARTENS, OLSON & BEAR, LLP

(57) ABSTRACT

Some aspects of the methods and compositions provided herein relate to the disruption of at least one CD4 gene in a cell, such as a CD4+ T cell. In some embodiments, the disruption comprises use of a CRISPR guide polynucleotide. Some embodiments also include the preparation and use of a cell having at least one disrupted CD4 gene and a chimeric antigen receptor (CAR). Some aspects of the methods and compositions provided herein relate to CARs, such as an anti-CD4 CAR or an anti-CD19 CAR, and use to treat
(Continued)

disorders including HIV, acute myeloid leukemia (AML), and acute lymphocytic leukemia (ALL).

20 Claims, 22 Drawing Sheets

Specification includes a Sequence Listing.

(51) Int. Cl.
*A61K 40/31* (2025.01)
*A61K 40/42* (2025.01)
*C07K 14/705* (2006.01)
*C12N 15/11* (2006.01)

(52) U.S. Cl.
CPC ........ *A61K 40/421* (2025.01); *A61K 40/4211* (2025.01); *C12N 15/111* (2013.01); *C12N 2310/20* (2017.05)

(58) Field of Classification Search
CPC ...................... C07K 16/1063; C07K 16/2812; A61K 40/11; A61K 40/31; A61K 40/421; A61K 40/4211; C12N 15/111; C12N 2310/20; C12N 9/22; C12N 2510/00; C12N 15/1138; A23B 11/1332; A61P 31/18; A61P 35/02; H10D 30/6745
See application file for complete search history.

(56) References Cited

U.S. PATENT DOCUMENTS

| | | | |
|---|---|---|---|
| 2004/0197809 | A1 | 10/2004 | Capon et al. |
| 2017/0015746 | A1 | 1/2017 | Jensen |
| 2017/0044240 | A1 | 2/2017 | Wagner et al. |
| 2017/0107286 | A1 | 4/2017 | Kochenderfer |
| 2018/0009891 | A1 | 1/2018 | Jensen |
| 2018/0066034 | A1 | 3/2018 | Ma et al. |
| 2018/0371052 | A1 | 12/2018 | Ma et al. |
| 2019/0062430 | A1 | 2/2019 | Wu et al. |
| 2019/0062735 | A1 | 2/2019 | Welstead et al. |
| 2019/0071657 | A1 | 3/2019 | Joung et al. |
| 2019/0071717 | A1 | 3/2019 | Zhang et al. |
| 2020/0000937 | A1 | 1/2020 | DiPersio et al. |

FOREIGN PATENT DOCUMENTS

| | | |
|---|---|---|
| WO | WO 17/027291 | 2/2017 |
| WO | WO 17/044776 | 3/2017 |
| WO | WO-2019106522 A1 * | 6/2019 |

OTHER PUBLICATIONS

Ansari-Lari, M. Ali, et al. "A gene-rich cluster between the CD4 and triosephosphate isomerase genes at human chromosome 12p13." Genome Research 6.4 (1996): 314-326 (Year: 1996).*

Korell, Felix, Trisha R. Berger, and Marcela V. Maus. "Understanding CAR T cell-tumor interactions: Paving the way for successful clinical outcomes." Med 3.8 (2022): 538-564. (Year: 2022).*

Tyznik, Aaron J., Joseph C. Sun, and Michael J. Bevan. "The CD8 population in CD4-deficient mice is heavily contaminated with MHC class II-restricted T cells." The Journal of experimental medicine 199.4 (2004): 559-565 (Year: 2004).*

Pearce, Erika L., Devon J. Shedlock, and Hao Shen. "Functional characterization of MHC class II-restricted CD8+ CD4- and CD8-CD4- T cell responses to infection in CD4-/- mice." The Journal of Immunology 173.4 (2004): 2494-2499 (Year: 2004).*

Casucci et al. 2011, Suicide gene therapy to increase the safety of chimeric antigen receptor-redirected T lymphocytes, Journal of Cancer, 2:378-382.

Hendel et al., Sep. 2015, Chemically modified guide RNAs enhance CRISPR-Cas genome editing in human primary cells, Nat Biotechnol. 33(9):985-989.

Chen et al., 2018, Functional interrogation of primary human T cells via CRISPR genetic editing, J Immunol, 201(5):1586-1598 and supplemental data.

Park et al., Feb. 2017, A genome-wide CRISPR screen identifies a restricted set of HIV host dependency factors, Nature Genetics, 49(2):193-203.

Wroblewska et al., Nov. 1, 2018, Protein barcodes enable high-dimensional single-cell CRISPR Screens, Cell, 175:1141-1155.

Hale, Malika et al., "Engineering HIV-Resistant, Anti-HIV Chimeric Antigen Receptor T Cells" Molecular Therapy, Mar. 2017, pp. 570-579, vol. 25, No. 3.

Sarafova, Sophia D. et al., "Deletion of the highly conserved functional region of the Cd4 enhancer NCE in RLMII cells using CRISPR/Cas9 reduces CD4 expression" The Journal of Immunology, May 2018, vol. 200, Supplement 1, 165.12.

International Search Report for PCT/US2020/023117 dated Aug. 14, 2020.

Ceja et al., Feb. 2024, CAR-T cell manufacturing: Major process parameters and next-generation strategies. J Exp Med. 221(2):e20230903.

Lee et al., Nov. 2023, CD8+ chimeric antigen receptor T cells manufactured in absence of CD4+ cells exhibit hypofunctional phenotype. J Immunother Cancer. 11(11):e007803.

Lisco et al., Feb. 15, 2021, Lost in Translation: Lack of CD4 Expression due to a Novel Genetic Defect, Journal of Infectious Diseases, 223:645-654.

Pearce et al., 2004, Functional Characterization of MHC Class II-Restricted CD+CD4- and CD8-CD4- T Cell Responses to Infection in CD4-/- Mice[1], Journal of Immunology, 173:2494-2499.

Sommermeyer et al., Feb. 2016, Chimeric antigen receptor-modified T cells derived from defined CD8+ and CD4+ subsets confer superior antitumor reactivity in vivo. Leukemia. 30(2):492-500.

Tyznik et al., Feb. 2004, The CD8 population in CD4-deficient mice is heavily contaminated with MHC class II-restricted T cells. J Exp Med. 99(4):559-565.

* cited by examiner

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: CD4-G1 (antisense)

<400> SEQUENCE: 1

agggactccc cggttcattg                                            20


<210> SEQ ID NO 2
<211> LENGTH: 20
<212> TYPE: DNA
<213> ORGANISM: Artificial Sequence
<220> FEATURE:
<223> OTHER INFORMATION: CD4-G2 (antisense)

<400> SEQUENCE: 2

gttcattgtg gccttgccga                                            20


<210> SEQ ID NO 3
<211> LENGTH: 20
<212> TYPE: DNA
<213> ORGANISM: Artificial Sequence
<220> FEATURE:
<223> OTHER INFORMATION: CD4-G3 (sense)

<400> SEQUENCE: 3
```

ggcaaggcca caatgaaccg 20

<210> SEQ ID NO 4
<211> LENGTH: 20
<212> TYPE: DNA
<213> ORGANISM: Artificial Sequence
<220> FEATURE:
<223> OTHER INFORMATION: CD4-G4 (antisense)

<400> SEQUENCE: 4
gcgcgatcat tcagcttgga 20

<210> SEQ ID NO 5
<211> LENGTH: 20
<212> TYPE: DNA
<213> ORGANISM: Artificial Sequence
<220> FEATURE:
<223> OTHER INFORMATION: CD4-G5 (antisense)

<400> SEQUENCE: 5
gtcagcgcga tcattcagct 20

<210> SEQ ID NO 6
<211> LENGTH: 20
<212> TYPE: DNA
<213> ORGANISM: Artificial Sequence
<220> FEATURE:
<223> OTHER INFORMATION: CD4-G6 (sense)

<400> SEQUENCE: 6
gaggtgcaat tgctagtgtt 20

<210> SEQ ID NO 7
<211> LENGTH: 20
<212> TYPE: DNA
<213> ORGANISM: Artificial Sequence
<220> FEATURE:
<223> OTHER INFORMATION: CD4-G7 (antisense)

<400> SEQUENCE: 7
cattcagctt ggatggacct 20

<210> SEQ ID NO 8
<211> LENGTH: 20
<212> TYPE: DNA
<213> ORGANISM: Artificial Sequence
<220> FEATURE:
<223> OTHER INFORMATION: CD4-G8 (antisense)

<400> SEQUENCE: 8
tcattcagct tggatggacc 20

<210> SEQ ID NO 9
<211> LENGTH: 249
<212> TYPE: PRT
<213> ORGANISM: Artificial Sequence
<220> FEATURE:
<223> OTHER INFORMATION: scFv for anti-CD4 chimeric antigen receptor

<400> SEQUENCE: 9

```
Asp Ile Val Met Thr Gln Ser Pro Ser Ser Leu Ala Val Ser Val Gly
1               5                   10                  15

Glu Lys Val Thr Met Ile Cys Lys Ser Ser Gln Ser Leu Leu Tyr Ser
            20                  25                  30

Thr Asn Gln Lys Asn Tyr Leu Ala Trp Tyr Gln Gln Lys Pro Gly Gln
```

-continued

```
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

Gly Gly Gly Gly Ser Gly Gly Gly Gly Ser Gly Gly Gly Gly Ser Glu
        115                 120                 125

Val Lys Leu Gln Glu Ser Gly Pro Glu Leu Val Lys Pro Gly Ala Ser
    130                 135                 140

Val Lys Met Ser Cys Lys Ala Ser Gly Tyr Thr Phe Thr Ser Tyr Val
145                 150                 155                 160

Ile His Trp Val Arg Gln Lys Pro Gly Gln Gly Leu Asp Trp Ile Gly
                165                 170                 175

Tyr Ile Asn Pro Tyr Asn Asp Gly Thr Asp Tyr Asp Glu Lys Phe Lys
            180                 185                 190

Gly Lys Ala Thr Leu Thr Ser Asp Lys Ser Ser Ser Thr Ala Tyr Met
        195                 200                 205

Glu Leu Ser Ser Leu Thr Ser Glu Asp Ser Ala Val Tyr Tyr Cys Ala
    210                 215                 220

Arg Glu Lys Asp Asn Tyr Ala Thr Gly Ala Trp Phe Ala Tyr Trp Gly
225                 230                 235                 240

Gln Gly Thr Thr Val Thr Val Ser Ser
                245
```

METHODS AND COMPOSITIONS FOR ENGINEERING CD4-DEFICIENT CAR T CELLS AND ANTI-CD4 CAR T CELLS AND USES THEREOF

CROSS-REFERENCE TO RELATED APPLICATIONS

This application is a U.S. National Phase Application of PCT International Application Number PCT/US2020/023117, filed on Mar. 17, 2020, designating the United States of America and published in the English language, which is an International Application of and claims the benefit of priority to U.S. Provisional Application No. 62/820,387, filed on Mar. 19, 2019. The disclosures of the above-referenced applications are hereby expressly incorporated by reference in their entireties.

STATEMENT REGARDING FEDERALLY SPONSORED R&D

This invention was made with government support under AI118500 awarded by the National Institutes of Health. The government has certain rights in the invention.

REFERENCE TO SEQUENCE LISTING

The present application is being filed along with a Sequence Listing in electronic format. The Sequence Listing is provided as a file entitled SeqList-SCRI-206NP, created Aug. 31, 2021, which is approximately 4 Kb in size. The information in the electronic format of the Sequence Listing is incorporated herein by reference in its entirety.

FIELD OF THE INVENTION

Some aspects of the methods and compositions provided herein relate to the disruption of at least one CD4 gene in a cell, such as a CD4+ T cell. In some embodiments, the disruption comprises use of a CRISPR guide polynucleotide. Some embodiments also include the preparation and use of a cell having at least one disrupted CD4 gene and a chimeric antigen receptor (CAR). Some aspects of the methods and compositions provided herein relate to CARs, such as an anti-CD4 CAR or an anti-CD19 CAR, and use to treat disorders including HIV, acute myeloid leukemia (AML), and acute lymphocytic leukemia (ALL).

BACKGROUND OF THE INVENTION

CD4+ T cells play a central role in the function of the immune system. They do so through their capacity to help B cells make antibodies, to induce macrophages to develop enhanced microbicidal activity, to recruit neutrophils, eosinophils, and basophils to sites of infection and inflammation, and, through their production of cytokines and chemokines, to orchestrate the full panoply of immune responses, including the regulation of the immune system. CD4 may also be expressed in other cell types. CD4 is also critical to the ability of some pathogens, for example HIV, to infect human cells. CD4 cells may also be infected by other pathogens, such as HTLV and EBV. In addition, there are situation in which CD4+ T cells cause disease. There are a variety of malignancies that are CD4+. CD4+ T cells may also play a role in some autoimmune and alloimmune conditions. Thus, there is a desire to develop new cellular therapies, which incorporate CD4-disruption and/or which target CD4 T cells.

SUMMARY OF THE INVENTION

Some embodiments of the methods and compositions provided herein include the following aspects.

Aspect 1: an isolated nucleic acid for disrupting a CD4 gene, comprising a clustered regularly interspaced short palindromic repeats (CRISPR) guide polynucleotide capable of hybridizing or configured to hybridize to a CD4 gene.

Aspect 2: the isolated nucleic acid of aspect 1, wherein the guide polynucleotide is capable of hybridizing or configured to hybridize to a sense strand of a CD4 gene.

Aspect 3: the isolated nucleic acid of aspect 1, wherein the guide polynucleotide is capable of hybridizing or configured to hybridize to an antisense strand of a CD4 gene.

Aspect 4: the isolated nucleic acid of any one of aspects 1-3, wherein the guide polynucleotide is capable of hybridizing or configured to hybridize to a first exon of a CD4 gene.

Aspect 5: the isolated nucleic acid of any one of aspects 1-3, wherein the guide polynucleotide is capable of hybridizing or configured to hybridize to a third exon of a CD4 gene.

Aspect 6: the isolated nucleic acid of any one of aspects 1-5, wherein the guide polynucleotide targets protospacer adjacent motif (PAM).

Aspect 7: the isolated nucleic acid of aspect 6, wherein the PAM comprises an NGG motif.

Aspect 8: the nucleic acid of any one of aspects 1-7 comprising a nucleotide sequence having at least 90%, 91%, 92%, 93%, 94%, 95%, 96%, 97%, 98%, or 99% sequence identity with a nucleotide sequence set forth in any one of SEQ ID NOS:01-08, or complement thereof.

Aspect 9: the nucleic acid of any one of aspects 1-8 comprising a nucleotide sequence having at least 90%, 91%, 92%, 93%, 94%, 95%, 96%, 97%, 98%, or 99% sequence identity with a nucleotide sequence set forth in SEQ ID NO:06, or complement thereof.

Aspect 10: the nucleic acid of any one of aspects 1-9 comprising a nucleotide sequence set forth in any one of SEQ ID NOS:01-08 or complement thereof.

Aspect 11: the nucleic acid of any one of aspects 1-10 comprising a nucleotide sequence set forth in SEQ ID NO:06 or complement thereof.

Aspect 12: the nucleic acid of any one of aspects 1-11, wherein the guide polynucleotide comprises RNA.

Aspect 13: a ribonucleoprotein (RNP) comprising the nucleic acid of any one of aspects 1-12.

Aspect 14: the RNP of aspect 13, wherein the RNP comprises a Cas9 protein.

Aspect 15: a method of preparing a genetically modified cell, comprising: introducing the RNP of aspect 13 or 14 into a cell.

Aspect 16: the method of aspect 15, further comprising introducing a second polynucleotide into the cell, wherein the second polynucleotide encodes a Cas9 protein.

Aspect 17: the method of aspect 16, wherein the introducing the RNP into the cell comprises electroporation or lipofection.

Aspect 18: a method of preparing a genetically modified cell, comprising: introducing a first polynucleotide encoding the nucleic acid of any one of aspects 1-12 into a cell; and introducing a second polynucleotide into the cell, wherein the second polynucleotide encodes a Cas9 protein.

Aspect 19: the method of aspect 18, wherein the introducing the first polynucleotide and/or the second polynucleotide into the cell comprises electroporation or lipofection.

Aspect 20: the method of any one of aspects 15-19, further comprising introducing a third polynucleotide into the cell, wherein the third polynucleotide encodes a chimeric antigen receptor (CAR).

Aspect 21: the method of aspect 20, wherein the CAR specifically binds to a CD4 protein.

Aspect 22: the method of aspect 20, wherein the CAR specifically binds to a CD19 protein.

Aspect 23: the method of aspect 20, wherein the CAR specifically binds to an HIV protein.

Aspect 24: the method of aspect 20, wherein the CAR comprises an antigen binding domain derived from an HIV neutralizing antibody.

Aspect 25: the method of aspect 24, wherein the HIV neutralizing antibody is selected from PGT128, PG9, or PGT145.

Aspect 26: the method of aspect any one of aspects 20-25, wherein the CAR is expressed from an inducible promoter.

Aspect 27: the method of any one of aspects 15-26, further comprising introducing a fourth polynucleotide into the cell, wherein the polynucleotide encodes a suicide gene system.

Aspect 28: the method of aspect 27, wherein the suicide gene system is a Herpes Simplex Virus Thymidine Kinase (HSVTK)/Ganciclovir (GCV) suicide gene system or an inducible Caspase suicide gene system.

Aspect 29: the method of any one of aspects 15-28, wherein the cell is mammalian.

Aspect 30: the method of any one of aspects 15-29, wherein the cell is human.

Aspect 31: the method of any one of aspects 15-30, wherein the cell expresses CD4.

Aspect 32: the method of any one of aspects 15-31, wherein the cell is a lymphocyte.

Aspect 33: the method of any one of aspects 15-32, wherein the cell is a T cell.

Aspect 34: the method of any one of aspects 15-33, wherein the cell is a primary cell.

Aspect 35: the method of any one of aspects 15-34, wherein the cell is isolated from peripheral blood mononucleated cells.

Aspect 36: the method of any one of aspects 15-35, wherein the cell expresses CD3 or CD8.

Aspect 37: the method of any one of aspects 15-36, wherein the cell is derived from a CD4+ cell, a natural killer cell, or a natural killer T cell.

Aspect 38: the method of any one of aspects 15-37, wherein the cell is ex vivo.

Aspect 39: a genetically modified cell prepared by the method of any one of aspects 15-38.

Aspect 40: a genetically modified cell comprising at least one CD4 gene disrupted by a clustered regularly interspaced short palindromic repeats (CRISPR) guide polynucleotide.

Aspect 41: the genetically modified cell of aspect 40, wherein the at least one CD4 gene is disrupted in a first exon of the CD4 gene.

Aspect 42: the genetically modified cell of aspect 40, wherein the at least one CD4 gene is disrupted in a third exon of the CD4 gene.

Aspect 43: the genetically modified cell of any one of aspects 40-42, wherein the at least one CD4 gene is disrupted by a CRISPR guide polynucleotide comprising a nucleotide sequence having at least 90%, 91%, 92%, 93%, 94%, 95%, 96%, 97%, 98%, or 99% sequence identity with a nucleotide sequence set forth in any one of SEQ ID NOS:01-08, or complement thereof.

Aspect 44: the genetically modified cell of any one of aspects 40-43, wherein the at least one CD4 gene is disrupted by a CRISPR guide polynucleotide comprising a nucleotide sequence having at least 90%, 91%, 92%, 93%, 94%, 95%, 96%, 97%, 98%, or 99% sequence identity with a nucleotide sequence set forth in SEQ ID NO:06, or complement thereof.

Aspect 45: the genetically modified cell of any one of aspects 40-44, wherein the at least one CD4 gene is disrupted by a CRISPR guide polynucleotide comprising a nucleotide sequence set forth in any one of SEQ ID NOS: 01-08 or complement thereof.

Aspect 46: the genetically modified cell of any one of aspects 40-45, wherein the at least one CD4 gene is disrupted by a CRISPR guide polynucleotide comprising a nucleotide sequence set forth in SEQ ID NO:06 or complement thereof.

Aspect 47: the genetically modified cell of any one of aspects 40-46, further comprising a chimeric antigen receptor (CAR).

Aspect 48: the genetically modified cell of aspect 47, wherein the CAR specifically binds to a CD4 protein.

Aspect 49: the genetically modified cell of aspect 47, wherein the CAR specifically binds to a CD19 protein.

Aspect 50: the genetically modified cell of aspect 47, wherein the CAR specifically binds to an HIV protein.

Aspect 51: the genetically modified cell of aspect 50, wherein the CAR comprises an antigen binding domain derived from an HIV neutralizing antibody.

Aspect 52: the genetically modified cell of aspect 51, wherein the HIV neutralizing antibody is selected from PGT128, PG9, or PGT145.

Aspect 53: the genetically modified cell of any one aspect 40-52, wherein the CAR is expressed from an inducible promoter.

Aspect 54: the genetically modified cell of any one of aspects 40-53, further comprising a polynucleotide encoding a suicide gene system.

Aspect 55: the genetically modified cell of aspect 54, wherein the suicide gene system is a Herpes Simplex Virus Thymidine Kinase (HSVTK)/Ganciclovir (GCV) suicide gene system or an inducible Caspase suicide gene system.

Aspect 56: the genetically modified cell of any one of aspects 40-55, wherein the cell is mammalian.

Aspect 57: the genetically modified cell of any one of aspects 40-56, wherein the cell is human.

Aspect 58: the genetically modified cell of any one of aspects 40-57, wherein the cell is a lymphocyte.

Aspect 59: the genetically modified cell of any one of aspects 40-58, wherein the cell is a T cell.

Aspect 60: the genetically modified cell of any one of aspects 40-59, wherein the cell is a primary cell.

Aspect 61: the genetically modified cell of any one of aspects 40-60, wherein the cell is isolated from peripheral blood mononucleated cells.

Aspect 62: the genetically modified cell of any one of aspects 40-61, wherein the cell expresses CD3 or CD8.

Aspect 63: the genetically modified cell of any one of aspects 40-62, wherein the cell is derived from a CD4+ cell, a natural killer cell, or a natural killer T cell.

Aspect 64: a pharmaceutical composition comprising the genetically modified cell of any one of aspects 40-63 and a pharmaceutically acceptable excipient.

Aspect 65: a population of genetically modified cells having increased resistance to HIV infection comprising the genetically modified cell of any one of aspects 40-63, wherein the resistance is increased compared to a cell in which at least one CD4 gene is not disrupted.

Aspect 66: a method of killing or inhibiting a population of CD4+ cells, comprising contacting the population of CD4+ cells with the genetically modified cell of any one of aspects 40-63.

Aspect 67: the method of aspect 66, wherein the population of CD4+ cells comprise HIV.

Aspect 68: the method of aspect 66, wherein the population of CD4+ cells comprise an acute myeloid leukemia (AML) cell, or an acute lymphocytic leukemia (ALL) cell.

Aspect 69: a method of reducing HIV-infected CD4+ cells, comprising contacting the population of CD4+ cells with the genetically modified cell of any one of aspects 40-63.

Aspect 70: the method of any one of aspects 66-69, wherein the population of CD4+ cells is autologous with the genetically modified cell.

Aspect 71: the method of any one of aspects 66-70, wherein the population of CD4+ cells is ex vivo.

Aspect 72: the method of any one of aspects 66-70, wherein the population of CD4+ cells is in vivo.

Aspect 73: a method of treating, inhibiting, or ameliorating a subject having an HIV infection acute myeloid leukemia (AML), or acute lymphocytic leukemia (ALL), comprising administering a population of cells comprising the genetically modified cell of any one of aspects 40-63 to the subject in need thereof.

Aspect 74: the method of aspect 72, wherein the genetically modified cell is autologous to the subject.

Aspect 75: the method of aspect 73 or 74, wherein the genetically modified cell comprises a chimeric antigen receptor (CAR).

Aspect 76: the method of aspect 75, wherein the CAR comprises an anti-CD4 CAR.

Aspect 77: the method of aspect 75, wherein the CAR specifically binds to a CD19 protein.

Aspect 78: the method of aspect 75, wherein the CAR specifically binds to an HIV protein.

Aspect 79: the method of aspect 75, wherein the CAR comprises an antigen binding domain derived from an HIV neutralizing antibody.

Aspect 80: the method of aspect 79, wherein the HIV neutralizing antibody is selected from PGT128, PG9, or PGT145.

Aspect 81: the method of any one of aspects 73-80, further comprising inducing expression of the CAR in the cell.

Aspect 82: the method of any one of aspects 73-80, further comprising inhibiting or reducing expression of the CAR in the cell.

Aspect 83: the method of any one of aspects 73-82, wherein expression of the CAR is inhibited or reduced after administration of the population of cells to the subject.

Aspect 84: the method of any one of aspects 73-82, wherein expression of the CAR is inhibited or reduced 1, 2, 3, 4, 5, 6, or 7 days after the administration of the population of cells to the subject.

Aspect 85: the method of any one of aspects 73-83, wherein expression of the CAR is inhibited or reduced 1, 2, 3, or 4 weeks after the administration of the population of cells to the subject.

Aspect 86: the method of any one of aspects 73-85, wherein the subject is mammalian.

Aspect 87: the method of any one of aspects 73-86, wherein the subject is human.

Aspect 88: the population of cells comprising the genetically modified cell of any one of aspects 40-63 for use in a medicament or for use in the treatment of HIV, acute myeloid leukemia (AML), or acute lymphocytic leukemia (ALL).

Aspect 89: use of a population of cells comprising the genetically modified cell of any one of aspects 40-63 in the preparation of a medicament for the treatment of HIV, acute myeloid leukemia (AML), or acute lymphocytic leukemia (ALL).

BRIEF DESCRIPTION OF THE DRAWINGS

FIG. 8 (upper row) is gated based on lymphocyte morphology (defined by forward scatter versus side scatter). FIG. 8 (lower row) is gated based on viable cells within the lymphocyte morphology gate.

FIG. 9 (top row) depicts the CAR expression within the live lymphocytes identified in FIG. 8, as measured by BFP expression, which is encoded downstream of the CAR. FIG. 9 ($2^{nd}$, $3^{rd}$ and $4^{th}$ rows) depict intracellular cytokine expression in the CAR expressing cells identified in the $1^{st}$ row, measured by flow cytometry. FIG. 9 ($2^{nd}$ row) depicts intracellular TNF-alpha expression as assessed by an anti-TNF-alpha antibody conjugated to PE. FIG. 9 ($3^{rd}$ row) depicts intracellular IL-2 expression as assessed by an anti-IL-2 antibody conjugated to PE-Cy7. FIG. 9 ($4^{th}$ row) depicts IFN-gamma expression as assessed by an anti-IFN-gamma antibody conjugated to APC.

FIG. 18 shows that more GFP positive cells survive when CD4 is disrupted.

DETAILED DESCRIPTION

Figure 1:
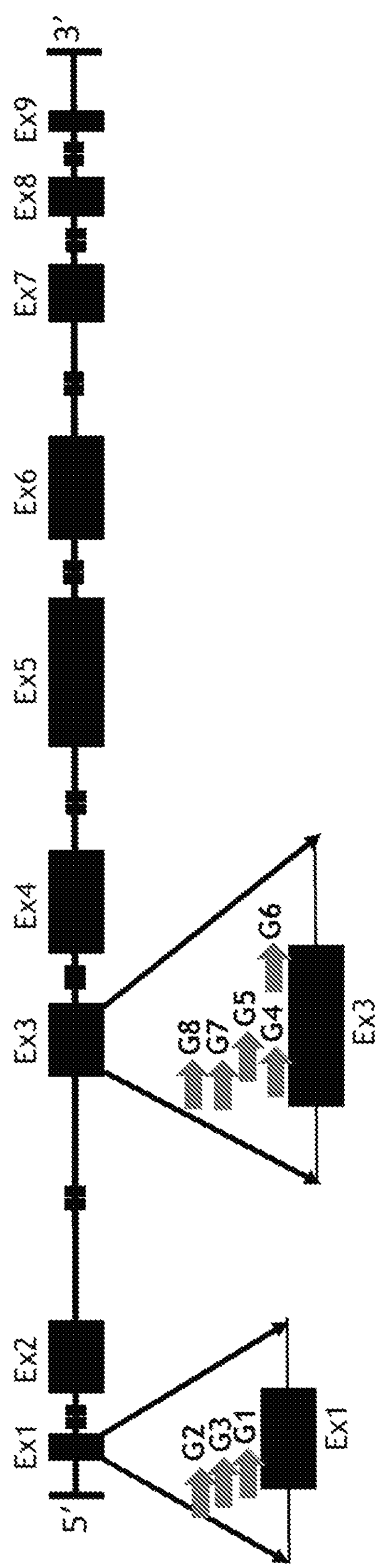
FIG. 1 depicts a schematic view of a CD4 gene with exons and introns, and the locations of six CRISPR guide polynucleotides, G1, G2, G3, G4, G5, G6, G7 and G8 in exons 1 and 3 of the CD4 gene.

Some embodiments provided herein relate to methods and compositions for the disruption of at least one CD4 gene in a cell, such as a CD4+ T cell. In some such embodiments, the disruption comprises the use of a CRISPR guide polynucleotide. Some embodiments also include the preparation and use of a cell having at least one disrupted CD4 gene and a chimeric antigen receptor (CAR) in a medicament. Some embodiments of the methods and compositions provided herein, for example, relate to cells such as T cells having CARs, such as an anti-CD4 CAR, or an anti-CD19 CAR, and the use thereof in a medicament, for instance to treat disorders including HIV, acute myeloid leukemia (AML), and CD4+ acute lymphocytic leukemia (ALL). In some embodiments, disruption of at least one CD4 gene in a cell, such as a CD4+ T cell, provides a cell having increased resistance to HIV infection compared to a cell in which at least one CD4 gene is not disrupted. Some embodiments include use of an anti-CD19 CAR to treat, inhibit, or ameliorate a disorder, such as acute lymphocytic leukemia (ALL), and/or HIV. In some such embodiments, CD4 expression would be problematic, such as in the use of allogenic T cells. As used herein, "disrupted" includes knocking-out a gene function of a gene such that a gene product is no longer expressed, and/or any gene product from a disrupted gene no longer has an activity.

Some embodiments provided herein include highly efficient disruption of a CD4 gene in a cell, such as a T cell, using certain CRISPR guide polynucleotides. In some embodiments, genetically modified T cells in which CD4 gene has been disrupted can also contain an anti-CD4 CAR. The genetically modified cells can be targeted against other cells, which express CD4. Some embodiments include the efficient depletion of a population of CD4+ cells with such genetically modified cells. Some embodiments include reducing HIV infection in a population of HIV-infected cells, and/or increasing the survival of cells in a population of HIV-infected cells. Some embodiments include targeting and killing AML cells. Some embodiments include targeting and killing ALL cells.

CD4+ T cell function is an important aspect of cell-based therapies, such as CD4+ CAR T cells. However, there may be some situations in which CD4-expression on CAR T cells may be problematic, such as: 1) in an HIV-infected patient in whom HIV can utilize CD4 to infect the CAR T cell; 2) when trying to produce an anti-CD4 CAR T cell product that would otherwise be expected to kill CD4+ anti-CD4 CAR T cells; or 3) when trying to produce a non-autologous therapeutic cell product.

Previously, it was not known whether a CD4+ T cell engineered to not express CD4 would continue to function like a CD4+ T cell. CD4 is a co-receptor of the T cell receptor (TCR), and together interact with antigen presenting cells. Therefore, CD4+ T cells engineered to not express CD4 would be expected to have a loss in TCR-related functions. However, as described herein, CD4+ CAR T cells that have been engineered to disrupt a CD4 gene, unexpectedly retain CD4+ functions including production of cytokines in the presence of cells expressing a target antigen and killing of cells expressing a target antigen.

CD4+ CAR T cells are important for the efficacy of current CAR T cell therapies. Combining CD4-disruption and an anti-CD4 CAR allows for production of an anti-CD4 CAR T cell product that still includes CD4−/CD8− cells that behave like CD4+ cells. Anti-CD4 CAR T cells may have potential benefit in many conditions, including in HIV-infection as a method to target and eradicate the reservoir of CD4+ HIV-infected cells.

Typically, successful treatments with CAR T cells have included the use of CD4+ CAR T cells. However, an anti-CD4 CAR T cells would be expected to target and kill CD4+ T cells. As indicated herein, CD4+ T cells containing an anti-CD4 CAR, engineered to not express CD4 and yet, which would still retain functions of a CD4+ T cell would be useful in certain therapeutic methods. In some such embodiments, it would be useful for the effect of the CAR T cell containing an anti-CD4 CAR to be limited, so that a treated subject may retain a population of CD4+ T cells after therapy. Thus, there is significant clinical interest in temporarily depleting CD4+ T cells in a subject. For example, temporarily depleting CD4+ T cells in a subject can help treat, ameliorate, or inhibit HIV by eliminating HIV-infected CD4 T cells in the subject. Temporarily depleting CD4+ T cells in a subject could also have applications in a wide range of therapies for autoimmune diseases, which involve or are dominated by autoreactive CD4 T cells; reducing cross reactivity in transplant patients; and treating, inhibiting, or ameliorating CD4+ malignancies. Embodiments provided herein include methods of producing anti-CD4 CAR T cells. By disrupting CD4, anti-CD4 CAR T cells can be produced, which do not express CD4, and therefore are protected from targeting and killing by anti-CD4 CAR T cells. Embodiments of the methods provided herein to disrupt CD4 gene in T cells were found to be surprisingly efficient. A substantially homogenous population of CD4-negative CART cells, which included both CD8+ and CD8− CART cells, was produced by transfecting cells with a ribonucleoprotein containing a CRISPR guide RNA to target the CD4 gene, shortly before transducing the modified cells with an anti-CD4 CAR. In addition, CD4 disrupted CAR T cells were found to have similar functions to CD4+ CAR T cells, as determined by expression of cytokines in target: effector assays. In some embodiments, it may be desirable to inhibit or reduce expression of an anti-CD4 CAR in a genetically modified cell after a treatment in a subject has been attained, such that not all CD4+ cells in a subject are depleted. Some such embodiments can include short-term depletion of CD4+ cells by regulating expression of anti-CD4 CAR in a genetically modified cell, such as expressing the CAR from an inducible promoter or in any other manner that can be pharmacologically regulated, or including a suicide system in the genetically modified cell to avoid long-term CD4+ cell depletion.

In some embodiments, genetically modified T cells in which the CD4 gene has been disrupted can also contain a CAR that targets human epitopes other than CD4, such as CD19, or pathogen-derived epitopes, such as HIV Env. There are several reasons that CAR T cells engineered not to express CD4 are potentially attractive for clinical applications: CD4+ CAR T cells engineered to not express CD4 will no longer react to the cognate antigen of the native T cell receptor, which may have advantages such as increasing the potency of the CAR-specific response; if allogenic CAR T cells are used, disrupting CD4 should help minimize CD4-mediated GVHD; and when CAR T cells are considered in HIV-infected individuals, disrupting CD4 is an efficient way to protect CAR T cells from HIV infection.

AML is a common malignancy that is difficult to treat and causes significant mortality. A limitation to treating AML is identifying a specific epitope on AML that can be safely targeted without significantly ablating the hematopoietic system or causing other off-target tissue toxicity. Most efforts to date have been focused on epitopes such as CD33 and CD123, although it is not yet clear whether these strategies are safe or effective. A subset of AML cells express CD4. CD4 expression is particularly increased in AML with rearrangements of the KMT2A (MLL) gene at 11q23. Moreover, the outcome of AML with high level CD4 expression is significantly worse than the survival in those with normal to low levels of CD4.

As disclosed herein, the ability of anti-CD4 CAR T cells to kill AML cells was tested in a killing assay. PBMC were stimulated and then transduced with an anti-CD4 CAR construct and expanded for approximately 3 weeks. In an example disclosed herein, anti-CD4 CAR T cells effectively targeted and killed an AML cells.

Certain aspects related to methods and compositions provided herein are included in U.S. patent Ser. No. 10/273,280; and US Pat. App. Pub. No. 2020/0000937 which are each expressly incorporated by reference in its entirety.

Definitions

As used herein, "nucleic acid", "nucleic acid molecule" or "polynucleotide" refer to molecules such as deoxyribonucleic acid (DNA) or ribonucleic acid (RNA), oligonucleotides, fragments generated by the polymerase chain reaction (PCR), and fragments generated by any of chemical synthesis, in vitro transcription, ligation, scission, endonuclease action, or exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and/or carbocyclic sugar analogs. Examples of modifications in a base moiety include alkylated purines, pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate. The term "nucleic acid molecule" also includes so-called "peptide nucleic acids," which comprise naturally-occurring or modified nucleic acid bases attached to a polyamide backbone. Nucleic acids can be either single stranded or double stranded.

As used herein, "coding strand" has its plain and ordinary meaning when read in light of the specification, and may include but is not limited to, for example, the DNA strand which has the same base sequence as the RNA transcript produced (although with thymine replaced by uracil). It is this strand, which contains codons, while the non-coding strand contains anti-codons.

As used herein, "coding for" or "encoding" are used herein, and refer to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system.

As used herein, "regulatory elements" have their plain and ordinary meaning when read in light of the specification, and may include but is not limited to, for example, a segment of a nucleic acid molecule, which is capable of increasing or decreasing the expression of specific genes within an organism, e.g., one that has the ability to affect the transcription and/or translation of an operably linked transcribable DNA molecule. Regulatory elements such as promoters (e.g. an MND promoter), leaders, introns, or transcription termination regions are DNA molecules that have gene regulatory activity and play an integral part in the overall expression of genes in living cells. Without being limiting, examples of regulatory elements can include, CAAT box, CCAAT box, Pribnow box, TATA box, SECIS element, mRNA Polyadenylation signals, A-box, Z-box, C-box, E-box, G-box, hormone responsive elements, such as insulin gene regulatory sequences, DNA binding domains, activation domains, or enhancer domains.

Some embodiments provided herein include a clustered regularly interspaced short palindromic repeats (CRISPR)/CAS system. A "CRISPR/CAS system" as described herein refers to a gene editing system in which expression of one or two component guide RNAs that are complimentary to a gene that is to be knocked out or expressed is necessary for a CRISPR/CAS system to function. Cas9 is an RNA-guided DNA endonuclease enzyme that associates with a one or two component guide RNA, allowing the complex to cleave a sequence that is complementary to the targeting portion of the guide RNA. In some embodiments, the basic components of CRISPR/CAS system comprise a target gene, such as CD4, a guide RNA, and a Cas9 endonuclease, derivative, or fragment thereof. In some embodiments, one aspect of applying CRISPR/Cas9 for gene editing is a system to deliver the guide RNAs efficiently to a wide variety of cell types. In some embodiments, delivery can include in vitro generated guide RNA as a nucleic acid, such as where the guide RNA generated by in vitro transcription or chemical synthesis. In some embodiments the nucleic acid encoding the guide RNA is rendered nuclease resistant by incorporation of modified bases, such as 2'O-methyl bases. In some embodiments, the guide RNA can be encapsulated into a ribonucleoprotein (RNP) complex.

Some embodiments provided herein include a CRISPR/Cpf1 system. A CRISPR/Cpf1 system includes the use of Cpf1, which is a single RNA guided endonuclease of a Class 2 CRISPR Cas9 system. As such, Cpf1, as a Class 2 effector, it relies on single component effector proteins such as Cas9 to mediate robust DNA interference with features that are distinct from Cas9. Cpf1 is a CRISPR-associated two-component RNA-programmable DNA nuclease. In some embodiments of the composition provided herein, the composition further comprises more than one sequence from a viral genome. In some embodiments, the more than one sequence from a viral genome encodes a promoter, a protein, a gene cassette for expressing a foreign gene, a clotting factor, an antibody or portion thereof (e.g., a binding portion or scFv), a CAS9 enzyme, a Cas9-VP64 enzyme, a nuclease, a protein whose functions are deficient in a disease, a recombination template for modification of a genomic site by homology directed repair or a cell surface protein. In some embodiments, the nuclease comprises Cpf1. More examples of CRISPR systems for embodiments provided herein are disclosed in U.S. Pat. Pub. Nos: 2019/0071717, 2019/0071657, 2019/0062735 which are each incorporated by reference herein in its entirety.

In some embodiments, the use of chemically modified CRISPR guide polynucleotides, such as RNAs is contemplated. Chemically-modified guide RNAs have been used in CRISPR-Cas genome editing in human primary cells (Hendel, A. et al., Nat Biotechnol. 2015 September; 33(9):985-9). Chemical modifications of guide RNAs can include modifications that confer nuclease resistance. Nucleases can be endonucleases, or exonucleases, or both. Some chemical modification, without limitations, include 2'-fluoro, 2'O-methyl, phosphorothioate dithiol 3'-3' end linkage, 2-amino-dA, 5-mehtyl-dC, C-5 propynyl-C, or C-5 propynyl-U, morpholino. These examples are not meant to be limiting and other chemical modifications and variants and modifications of these exemplary embodiments are also contemplated.

As used herein, "chimeric antigen receptors" (CARs) refer to genetically engineered protein receptors, which can confer specificity onto an immune effector cell, such as for example, a T-cell. Without being limiting, the use of CAR bearing T-cells can promote in vivo expansion and activation. The CARs can also be designed to redirect T-cells to target cells that express specific cell-surface antigens, where they can activate lymphocytes, such as T-cells, upon target recognition. The CARs graft the specificity of a monoclonal antibody or binding fragment thereof or scFv onto a T-cell, with the transfer of their coding sequence facilitated by vectors. In order to use CARs as a therapy for a subject in need, a technique called adoptive cell transfer is used in which T-cells are removed from a subject and modified so that they can express the CARs that are specific for an antigen. The T-cells, which can then recognize and target an antigen, are reintroduced into the patient. In some embodiments, CAR expressing lymphocytes are described, wherein the CAR expressing lymphocyte can be delivered to a subject to target specific cells. In some embodiments, the lymphocyte can express two CARs for bi-specificity. In some embodiments, the lymphocyte can express a CAR and a specific T-cell receptor (TcR) for bi-specificity. A TcR is a molecule on the surface of T lymphocytes or T-cells that can recognize antigens. In some embodiments, the lymphocyte can express a bi-specific CAR for bi-specificity, wherein the bi-specific CAR. The structure of the CAR can comprise fusions of single-chain variable fragments (scFv) that are derived from monoclonal antibodies that are attached to transmembrane and cytoplasmic signaling domains. Most CARs can include an extracellular scFv that is linked to an intracellular CD3 domain (first generation CAR). Additionally, the scFv can be linked to a co-stimulatory domain, such as CD28 and/or 4-1BB, which can increase their efficacy in the therapy of a subject in need (second generation CAR). When T-cells express this molecule they can recognize and kill target cells that express a specific antigen targeted by the CAR.

In some embodiments, promoters used herein can be inducible or constitutive promoters. Without being limiting, inducible promoters can include, for example, a tamoxifen inducible promoter, tetracycline inducible promoter, or a doxocycline inducible promoter (e.g. tre) promoter. Constitutive promoters can include, for example, SV40, CMV, UBC, EF1 alpha, PGK, or CAGG. In some embodiments, the promoter is a tamoxifen inducible promoter, a tetracycline inducible promoter, or a doxocycline inducible promoter (e.g. tre) promoter. In some embodiments provided herein, expression of a protein is induced by tamoxifen and/or its metabolites. Metabolites for tamoxifen are active metabolites such as 4-hyroxytamoxifen (afimoxifene) and N-desmethyl-4-hydroxytamoxifen (endoxifen), which can have 30-100 times more affinity with an estrogen receptor than tamoxifen itself. In some embodiments, the tamoxifen metabolites are 4-hyroxytamoxifen (afimoxifene) and/or N-desmethyl-4-hydroxytamoxifen (endoxifen). In some embodiments, an inducible promoter is designed and/or modified to provide for a low level of basal activity, a high level of inducibility, and/or a short time for reversibility. In other embodiments the CAR can be engineered so that expression can be regulated with pharmacologic agents in a manner that is independent from promoter function, such as but not limited to systems described that use rapamycin, rapamycin analogues, or HCV NS3 protease inhibitors.

As used herein, "suicide gene therapy," "suicide genes" and "suicide gene systems" can refer to methods to destroy a cell through apoptosis, which requires a suicide gene that will cause a cell to kill itself by apoptosis. Suicide gene therapy can be used to increase the safety of the genetically modified immune cells and manage the adverse events that can occur following infusion of genetically modified immune cells. There are several methods for suicide gene therapy. In some embodiments, genetically modified cells can further be modified ex vivo with a suicide gene. Without being limiting, the suicide gene can be a gene encoding for a factor that is able to convert at a cellular level a non-toxic prodrug into a toxic compound. The prodrug can be administrated to a subject, and the prodrug can selectively eliminate suicide gene modified genetically modified cells. Suicide systems using the herpes simplex thymidine kinase (Hsv-tk)/ganciclovir (GCV) suicide system have been described. (Casucci et al. 2011, Journal of Cancer 2011, 2; hereby expressly incorporated by reference in its entirety). In some embodiments, the suicide gene system is a Herpes Simplex Virus Thymidine Kinase (HSVTK)/Ganciclovir (GCV) suicide gene system or an inducible Caspase suicide gene system.

As used herein, "subject" or "patient," refers to any organism upon which the embodiments described herein may be used or administered, e.g., for experimental, diagnostic, prophylactic, and/or therapeutic purposes. Subjects or patients include, for example, animals. In some embodiments, the subject is mice, rats, rabbits, non-human primates, and humans. In some embodiments, the subject is a cow, sheep, pig, horse, dog, cat, primate or a human.

As used herein, "treatment" and "treating," depending on the context can refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment or therapy include those already with the condition, as well as, those prone to have the condition or those in whom the condition is to be prevented.

Certain Polynucleotides

Some embodiments of the methods and compositions provided herein include disrupting a CD4 gene in a cell. For example, a CD4 gene can be disrupted by an insertion, deletion or mutation in the CD4 gene. In some embodiments of the methods and compositions provided herein can disrupt one or all alleles of a CD4 gene in a cell. For example, in a diploid genome, methods and compositions provided herein can disrupt one or both alleles of a CD4 gene in a cell. In some embodiments, disruption of a CD4 gene can inhibit the expression of a functional CD4 protein in a cell. For example, disruption of a CD4 gene can result in no expression of a CD4 protein, reduced expression of a CD4 protein, or expression of a non-functional variant of a CD4 protein or fragment thereof. In some embodiments, a non-functional variant of CD4 protein may not bind or not efficiently bind with a ligand or receptor that specifically binds to a functional CD4 protein. In some embodiments, a non-functional variant of a CD4 protein or fragment thereof may not bind or efficiently bind with a ligand-binding domain of a chimeric antigen receptor. In some embodiments, disruption of a CD4 gene can include the use of isolated nucleic acids for disrupting at least one CD4 gene in a cell. Some isolated nucleic acids include clustered regularly interspaced short palindromic repeats (CRISPR) guide polynucleotides capable of hybridizing or configured to hybridize to a CD4 gene. In some embodiments, the guide polynucleotide comprises RNA.

In some embodiments, the guide polynucleotide is capable of hybridizing or configured to hybridize to a sense strand of a CD4 gene. In some embodiments, the guide polynucleotide is capable of hybridizing or configured to hybridize to an antisense strand of a CD4 gene. In some embodiments, the guide polynucleotide is capable of hybridizing or configured to hybridize to any portion of a CD4 gene, which would disrupt expression of the gene, for example, a regulatory element of the gene, such as a promoter, an exon, a splice site, or an intron. In some such embodiments, the guide polynucleotide is capable of hybridizing or configured to hybridize to an exon of the CD4 gene, such as a first exon, a second exon, a third exon, a fourth exon, a fifth exon, a sixth exon, a seventh exon, an eighth exon or a ninth exon of the CD4 gene. In some embodiments, the guide polynucleotide is capable of hybridizing or configured to hybridize to a first exon of a CD4 gene. In some embodiments, the guide polynucleotide is capable of hybridizing or configured to hybridize to a third exon of a CD4 gene.

In some embodiments, the guide polynucleotide can include a nucleotide sequence having at least a certain percentage identity with a nucleotide sequence set forth in any one of SEQ ID NOS:01-08, or a complement thereof. In some embodiments, the guide polynucleotide comprises a nucleotide sequence having at least 70%, 75%, 80%, 85%, 90%, 95%, 96%, 97%, 98%, 99%, or 100%, sequence identity to any one of SEQ ID NOS:01-08 or a complement thereof or a percentage of sequence identity that is within a range defined by any two of the aforementioned percentages. In some embodiments, the guide polynucleotide comprises a nucleotide sequence having at least a certain percentage identity with a nucleotide sequence set forth in SEQ ID NO:06 or complement thereof. In some embodiments, the guide polynucleotide comprises a nucleotide sequence having at least a 70%, 75%, 80%, 85%, 90%, 95%, 96%, 97%, 98%, 99%, 100%, sequence identity to SEQ ID NO:06 or its complement or a sequence identity that is within a range defined by any two of the aforementioned percentages. In some embodiments, the guide polynucleotide can include a nucleotide sequence set forth in any one of SEQ ID NOS: 01-08, or the complement thereof. In some embodiments, the guide polynucleotide can include a nucleotide sequence set forth in SEQ ID NO:06, or the complement thereof.

Certain Methods of Preparing Cells

Some embodiments of the methods and compositions provided herein include methods of preparing genetically modified cells. Some such embodiments can include use of gene targeting systems to specifically modify a CD4 locus in a cell. Some embodiments include the use of a clustered regularly interspaced short palindromic repeats (CRISPR) system, such as a CRISPR/Cas9 system with guide polynucleotides.

In some embodiments, genetically modified cells can be prepared by introducing a CRISPR guide polynucleotide and a Cas9 protein into a target cell. In some embodiments, one or more vectors encoding the CRISPR guide polynucleotide, and/or encoding the Cas9 protein can be introduced into the target cell. In some embodiments, the CRISPR guide polynucleotide, and/or encoding the Cas9 protein can be introduced directly into the target cell. For example, a ribonucleoprotein (RNP) can be prepared that comprises the CRISPR guide polynucleotide and/or Cas9 protein can be introduced into the target cell. Methods of introducing vectors, or RNPs into a cell can include lipofection or electroporation.

In some embodiments, the guide polynucleotide can include a guide polynucleotide disclosed herein. In some embodiments, the guide polynucleotide can include a nucleotide sequence having at least a certain percentage identity with a nucleotide sequence set forth in any one of SEQ ID NOS:01-08 or complement thereof. In some embodiments, the certain percentage identity with a nucleotide sequence set forth in any one of SEQ ID NOS:01-08, or complement thereof can be at least 70%, 75%, 80%, 85%, 90%, 95%, 96%, 97%, 98%, 99%, 100%, or any percentage between any two of the foregoing percentages. In some embodiments, the guide polynucleotide can include a nucleotide sequence having at least a certain percentage identity with a nucleotide sequence set forth in SEQ ID NO:06 or complement thereof. In some embodiments, the certain percentage identity with a nucleotide sequence set forth in SEQ ID NO:06, or complement thereof can be at least 70%, 75%, 80%, 85%, 90%, 95%, 96%, 97%, 98%, 99%, 100%, or any percentage between any two of the foregoing percentages. In some embodiments, the guide polynucleotide can include a nucleotide sequence set forth in any one of SEQ ID NOS:01-08, or the complement thereof. In some embodiments, the guide polynucleotide can include a nucleotide sequence set forth in SEQ ID NO:06, or the complement thereof.

Some embodiments of the methods and compositions provided herein include methods of preparing genetically modified cells, which comprise a CAR. Some such embodiments can include introducing a polynucleotide encoding a CAR into a cell. In some embodiments, the CAR comprises an antigen binding domain, which specifically binds to a CD4 protein, or a CD19 protein. Examples of anti-CD4 CARs or anti-CD19 CARs are disclosed in U.S. Pat. No. 9,951,118; U.S. 2018/0371052; U.S. 2017/0107286; U.S. 2019/0062430, which are each expressly incorporated by reference in its entirety.

In some embodiments, the polynucleotide encoding a CAR includes an inducible promoter, such that expression of the CAR in a cell can be induced, or in manner that can be pharmacologically regulated.

Some embodiments of the methods and compositions provided herein include methods of preparing genetically modified cells also include introducing at polynucleotide encoding a suicide gene system into a cell. In some embodiments, the suicide gene system is a Herpes Simplex Virus Thymidine Kinase (HSVTK)/Ganciclovir (GCV) suicide gene system or an inducible Caspase suicide gene system.

In some embodiments, the cell is mammalian. In some embodiments, the cell is human. In some embodiments, the cell expresses CD4 protein prior to disruption of a CD4 gene. In some embodiments, the cell is a lymphocyte. In some embodiments, the cell is a T cell. In some embodiments, the cell is a primary cell. In some embodiments, the cell is isolated from peripheral blood mononucleated cells. In some embodiments, the cell expresses CD3. In some embodiments, the cell expresses CD8. In some embodiments, the cell is in vivo. In some embodiments, the cell is ex vivo.

Some embodiments of the methods and compositions provided herein include a cell prepared by any method disclosed herein.

Certain Cells

Some embodiments of the methods and compositions provided herein include a genetically modified cell, which can be used in a medicament. In some embodiments, the genetically modified cell comprises at least one disrupted CD4 gene. In some such embodiments, the CD4 gene has been disrupted by a CRISPR guide polynucleotide provided herein.

In some embodiments, the at least one CD4 gene is disrupted in a first exon of the CD4 gene. In some embodiments, the at least one CD4 gene is disrupted in a third exon of the CD4 gene. In some embodiments, the at least one CD4 gene is disrupted by a CRISPR guide polynucleotide comprising a nucleotide sequence having at least 90% sequence identity with a nucleotide sequence set forth in any one of SEQ ID NOS:01-08 or complement thereof. In some embodiments, the at least one CD4 gene is disrupted by a CRISPR guide polynucleotide comprising a nucleotide sequence having at least 90% sequence identity with a nucleotide sequence set forth in SEQ ID NO:06 or complement thereof. In some embodiments, the at least one CD4 gene is disrupted by a CRISPR guide polynucleotide comprising a nucleotide sequence set forth in any one of SEQ ID NOS:01-08 or complement thereof. In some embodiments, the at least one CD4 gene is disrupted by a CRISPR guide polynucleotide comprising a nucleotide sequence set forth in SEQ ID NO:06 or complement thereof.

Some embodiments of the methods and compositions provided herein include a genetically modified cell containing a CAR, which can be used in a medicament. In some embodiments, the CAR comprises an antigen binding domain, which specifically binds to a CD4 protein. Examples of anti-CD4 CARs are disclosed in U.S. 2018/0371052, which is hereby expressly incorporated by reference in its entirety. In some embodiments, a polynucleotide encoding a CAR includes an inducible promoter, such that expression of the CAR in a cell can be induced, or in any other manner that can be pharmacologically regulated In some embodiments, the CAR comprises an anti CD19 CAR. In some embodiments, the CAR comprises an anti-HIV CAR. In some such embodiments, the anti-HIV CAR can include a scFv derived from an anti-HIV neutralizing antibody. Examples of such antibodies include PGT128, PG9 and PGT145. Examples of methods and compositions that can be included in the embodiments provided herein are disclosed in U.S. 2017/0044240 which is expressly incorporated by reference in its entirety. More examples of CARs that can be included in the embodiments provided herein are disclosed in U.S. 2018/0009891, 2017/0015746; U.S. Pat. No. 9,951,118; U.S. 2018/0371052; U.S. 2017/0107286; U.S. 2019/0062430; and WO 2017/027291 which are each expressly incorporated by reference in its entirety.

Some embodiments of the methods and compositions provided herein include a genetically modified cell containing a suicide gene system. In some embodiments, the suicide gene system is a Herpes Simplex Virus Thymidine Kinase (HSVTK)/Ganciclovir (GCV) suicide gene system or an inducible Caspase suicide gene system.

In some embodiments, the cell is mammalian. In some embodiments, the cell is human. In some embodiments, the cell expresses CD4 protein prior to disruption of a CD4 gene. In some embodiments, the cell is a lymphocyte. In some embodiments, the cell is a T cell. In some embodiments, the cell is a primary cell. In some embodiments, the cell is isolated from peripheral blood mononucleated cells. In some embodiments, the cell expresses CD3. In some embodiments, the cell expresses CD8. In some embodiments, the cell is derived from a CD4+ cell, a natural killer cell, or a natural killer T cell. In some embodiments, the cell is in vivo. In some embodiments, the cell is ex vivo.

Some embodiments of the methods and compositions provided herein include a pharmaceutical composition comprising a genetically modified cell disclosed herein and a pharmaceutically acceptable excipient.

Certain Methods of Killing or Inhibiting Cells

Some embodiments of the methods and compositions provided herein include a method of killing or inhibiting a population of CD4+ cells, comprising contacting the population of CD4+ cells with a genetically modified cell disclosed herein. In some such embodiments, the population of CD4+ cells comprises a virus. In some embodiments, the virus is HIV. In some embodiments, the population of CD4+ cells is autologous with the genetically modified cell. In some embodiments, the population of CD4+ cells is non-autologous with the genetically modified cell. In some embodiments, the population of CD4+ cells and/or the genetically modified cell is ex vivo. In some embodiments, the population of CD4+ cells and/or the genetically modified cell is in vivo.

Some embodiments of the methods and compositions provided herein include a method of reducing or inhibiting or ameliorating HIV replication in a population of HIV-infected CD4+ cells. Some such embodiments include contacting the population of CD4+ cells with a genetically modified cell disclosed herein. In some embodiments, the population of CD4+ cells is autologous with the genetically modified cell. In some embodiments, the population of CD4+ cells is not autologous with the genetically modified cell. In some embodiments, the population of CD4+ cells and/or the genetically modified cell is ex vivo. In some embodiments, the population of CD4+ cells and/or the genetically modified cell is in vivo. In some embodiments, the level of HIV replication in a population of HIV-infected CD4+ cells contacted with a genetically modified cell is reduced compared to the level of HIV replication in a population of HIV-infected CD4+ cells not contacted with the genetically modified cell by at least 1%, 3%, 5%, 10%, 15%, 20%, 25% 30%, 50%, 75%, 90%, 99%, 100%, or is reduced by a percentage that is within a range defined by any two of the aforementioned percentages.

Some embodiments of the methods and compositions provided herein include a method of increasing survival of a population of HIV-infected CD4+ cells. Some such embodiments include contacting the population of CD4+ cells with a genetically modified cell disclosed herein. In some embodiments, the population of CD4+ cells is autologous with the genetically modified cell. In some embodiments, the population of CD4+ cells is not autologous with the genetically modified cell. In some embodiments, the population of CD4+ cells and/or the genetically modified cell is ex vivo. In some embodiments, the population of CD4+ cells and/or the genetically modified cell is in vivo. In some embodiments, the survival of a population of HIV-infected CD4+ cells contacted with a genetically modified cell is increased compared to the survival of a population of HIV-infected CD4+ cells not contacted with the genetically modified cell by at least 1%, 3%, 5%, 10%, 15%, 20%, 25% 30%, 50%, 75%, 90%, 99%, 100%, or any percentage between any two of the foregoing percentages.

Some embodiments of the methods and compositions provided herein include methods of treating, inhibiting, or ameliorating an HIV infection in a subject having an HIV infection. Some such embodiments include administering a population of cells comprising a genetically modified cell disclosed herein to a subject in need thereof. In some embodiments, the genetically modified cell is autologous to the subject. In some embodiments, the genetically modified cell is not autologous to the subject. In some embodiments, the subject is mammalian. In some embodiments, the subject is human. In some embodiments, the subject is selected as one to receive a therapy for HIV infection. In some embodiments, the selection of said subject is performed by clinical and/or diagnostic evaluation. Such diagnostic or clinical evaluation may be made by assessing the presence and/or amount of HIV infection in said subject, such as by analysis of the presence of HIV virus, HIV proteins or HIV nucleic acids in said subject.

In some embodiments, the genetically modified cell comprises a CAR. In some embodiments, the CAR comprises an anti-CD4 CAR, and/or an anti-CD19 CAR.

Some embodiments also include inducing expression of the CAR in the cell. For example, a polynucleotide encoding a CAR can include an inducible promoter, or be engineered in manner that allows it to be regulated with a pharmacologic agent. In some such embodiments, a subject can be administered an inductor to induce or inhibit expression of a CAR in a cell containing the polynucleotide encoding the CAR.

Some embodiments also include inducing comprising inhibiting or reducing expression of the CAR in a cell. In some such embodiments, administration of an inductor to induce expression of a CAR in a cell containing the polynucleotide encoding the CAR can be stopped, or a dosage reduced. In some embodiments, an inhibitor to reduce expression of a CAR in a cell can be administered to a subject. In some embodiments, expression of the CAR is inhibited or reduced after administration of the population of cells to the subject. In some embodiments, expression of the CAR is inhibited or reduced for a period of at least 1, 2, 3, 4, 5, 6, or 7 days or a period of time between any two of the foregoing periods, after the administration of the population of cells to the subject. In some embodiments, expression of the CAR is inhibited or reduced for a period of at least 1, 2, 3, or 4 weeks or a period of time between any two of the foregoing periods, after the administration of the population of cells to the subject.

Some embodiments also include methods of therapy in combination with additional therapies. For example, HIV management can include the use of anti-retroviral drugs in order to control HIV infection. By way of example and not of limitation, classes of drugs for the treatment, therapy, or management of HIV can include entry or fusion inhibitors (e.g., maraviroc or enfuvirtide), nucleoside reverse transcriptase inhibitors (e.g., zidovudine, abicavir, lamivudine, emtricitabine, or tenofovir), Non-nucleoside reverse transcriptase inhibitors (e.g., nevirapine, efavirenz, etravirine, or rilpivirine), integrase inhibitors (e.g., elvitegravir or dolutegravir), and/or protease inhibitors (e.g., Lopinavir, Indinavir, Nelfinavir, Amprenavir, Ritonavir, Darunavir, or Atazanavir). Combinational therapy with any of the disclosed classes of drugs in conjunction with one or more of the CAR-containing T-cells described herein can also be used for the treatment and management of HIV.

Certain Kits

Some embodiments of the methods and compositions provided herein include kits for preparing a genetically modified cell. Some such kits can include an isolated polynucleotide for disrupting a CD4 gene in a cell. In some embodiments, the isolated polynucleotide comprises a CRISPR guide polynucleotide comprising a nucleotide sequence having at least 90%, 91%, 92%, 93%, 94%, 95%, 96%, 97%, 98%, or 99% sequence identity with a nucleotide sequence set forth in any one of SEQ ID NOS:01-08, or complement thereof. In some embodiments, the at least one CD4 gene is disrupted by a CRISPR guide polynucleotide comprising a nucleotide sequence having at least 90%, 91%, 92%, 93%, 94%, 95%, 96%, 97%, 98%, or 99% sequence identity with a nucleotide sequence set forth in SEQ ID NO:06, or complement thereof. In some embodiments, the at least one CD4 gene is disrupted by a CRISPR guide polynucleotide comprising a nucleotide sequence set forth in any one of SEQ ID NOS:01-08 or complement thereof. In some embodiments, at least one CD4 gene is disrupted by a CRISPR guide polynucleotide comprising a nucleotide sequence set forth in SEQ ID NO:06 or complement thereof. Some embodiments can also include a polynucleotide encoding a Cas9 protein. Some embodiments can also include a Cas9 protein.

EXAMPLES

Example 1—CRISPR-Cas9 Mediated Disruption of CD4 in T Cells

This example relates to disruption of the CD4 gene in cells using Cas9 and CRISPR guide polynucleotides. Six CRISPR guides were designed to target the CD4 gene. FIG. 1 illustrates the targeted location for each CRISPR guide, and TABLE 1 lists the sequence of each CRISPR guides.

TABLE 1

| Guide (strand) | SEQ ID NO | Sequence |
|---|---|---|
| CD4-G1 (antisense) | SEQ ID NO: 01 | AGGGACTCCC CGGTTCATTG |
| CD4-G2 (antisense) | SEQ ID NO: 02 | GTTCATTGTG GCCTTGCCGA |
| CD4-G3 (sense) | SEQ ID NO: 03 | GGCAAGGCCA CAATGAACCG |
| CD4-G4 (antisense) | SEQ ID NO: 04 | GCGCGATCAT TCAGCTTGGA |
| CD4-G5 (antisense) | SEQ ID NO: 05 | GTCAGCGCGA TCATTCAGCT |
| CD4-G6 (sense) | SEQ ID NO: 06 | GAGGTGCAAT TGCTAGTGTT |
| CD4-G7 (antisense) | SEQ ID NO: 07 | CATTCAGCTT GGATGGACCT |

TABLE 1-continued

| Guide (strand) | SEQ ID NO | Sequence |
|---|---|---|
| CD4-G8 (antisense) | SEQ ID NO: 08 | TCATTCAGCT TGGATGGACC |

Figure 2A:
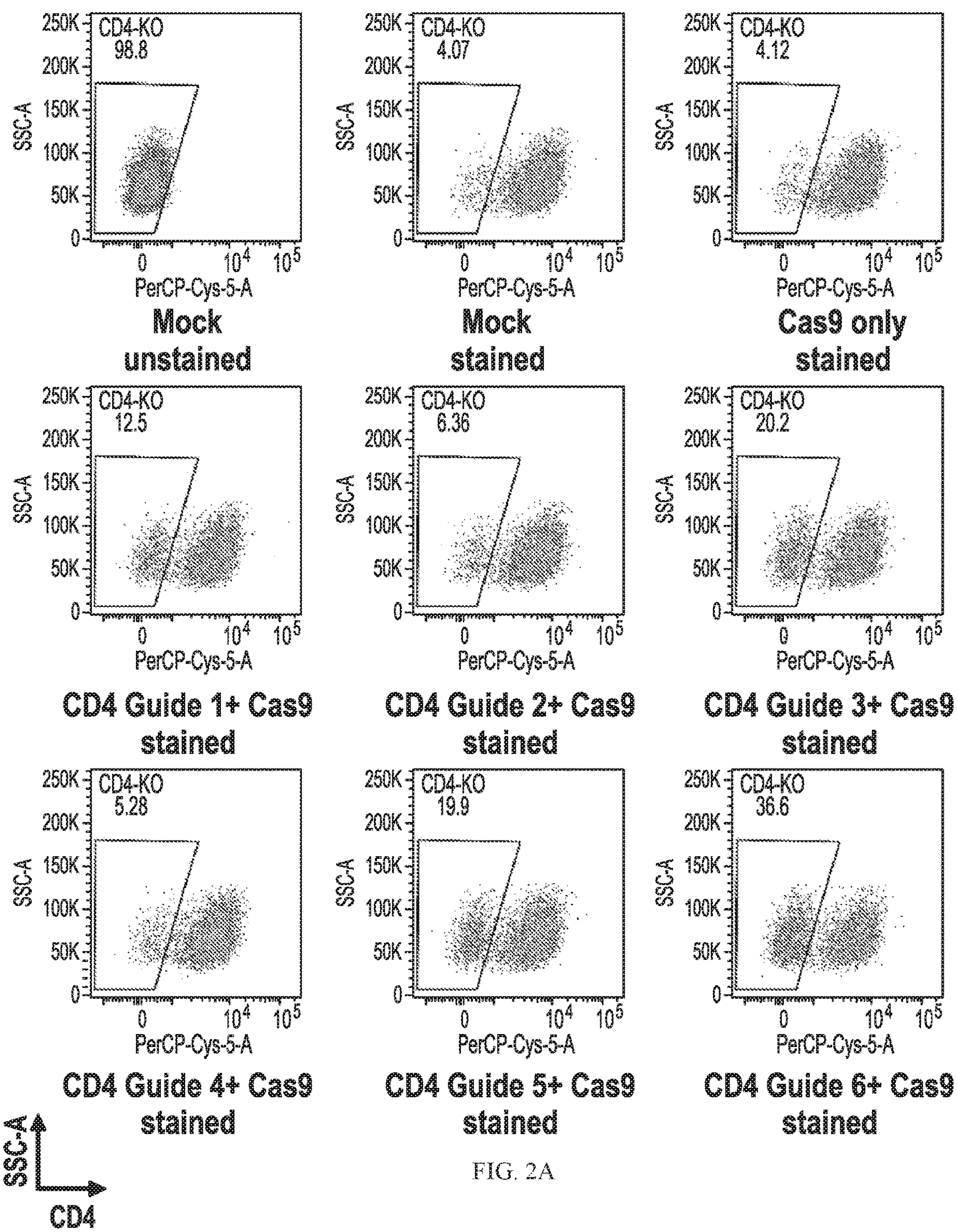
FIG. 2A depicts flow cytometry data with CD4+ cell line stained for CD4 on the X-axis plotted against side scatter area (SSC-A) on the Y-axis, in which cells were untreated (mock), treated with Cas9 only, or treated with Cas9 and a CRISPR guide polynucleotide (G1, G2, G3, G4, G5 and G6).

Each guide was used to disrupt CD4 gene in A3.01 cells (human T cell line) which express high levels of CD4. Guides were introduced into the cells as a ribonucleoprotein (RNP) via electroporation. The relative efficacy of the guides was evaluated by their ability to decrease CD4 expression on the cell surface, as measured by flow cytometry. Data was generated at day 7 post Cas9+guide transfection. Controls included un-modified (no CRISPR/Cas9 treatment) cells with no staining for CD4, unmodified cells (no CRISPR/Cas9 treatment) stained for CD4, and cells treated with Cas9 only without a guide and stained for CD4 (FIG. 2A, top row). In the absence CRISPR/Cas9, ~96% of cells were CD4+. In the presence of different CRISPR/Cas9 guides targeting CD4, CD4 expression was decreased to ~94-64% in cells treated with various guides (FIG. 2A, middle and bottom rows). A priori, it was not known which guide would perform the best. Surprisingly, some guides that were predicted to disrupt CD4 expression were not efficient in disrupting CD4 expression. Indeed, Guide 3 and Guide 6 both had significantly more activity to disrupt CD4 gene than the other guides. Guide 6 performed the best, and reduced CD4 expression to 64%.

Guide 3 and Guide 6 were tested for their ability to disrupt CD4 in primary lymphocytes. The relative efficacy of the two guides was evaluated by their ability to decrease CD4 expression on the cell surface, as measured by flow cytometry.

Figure 2B:
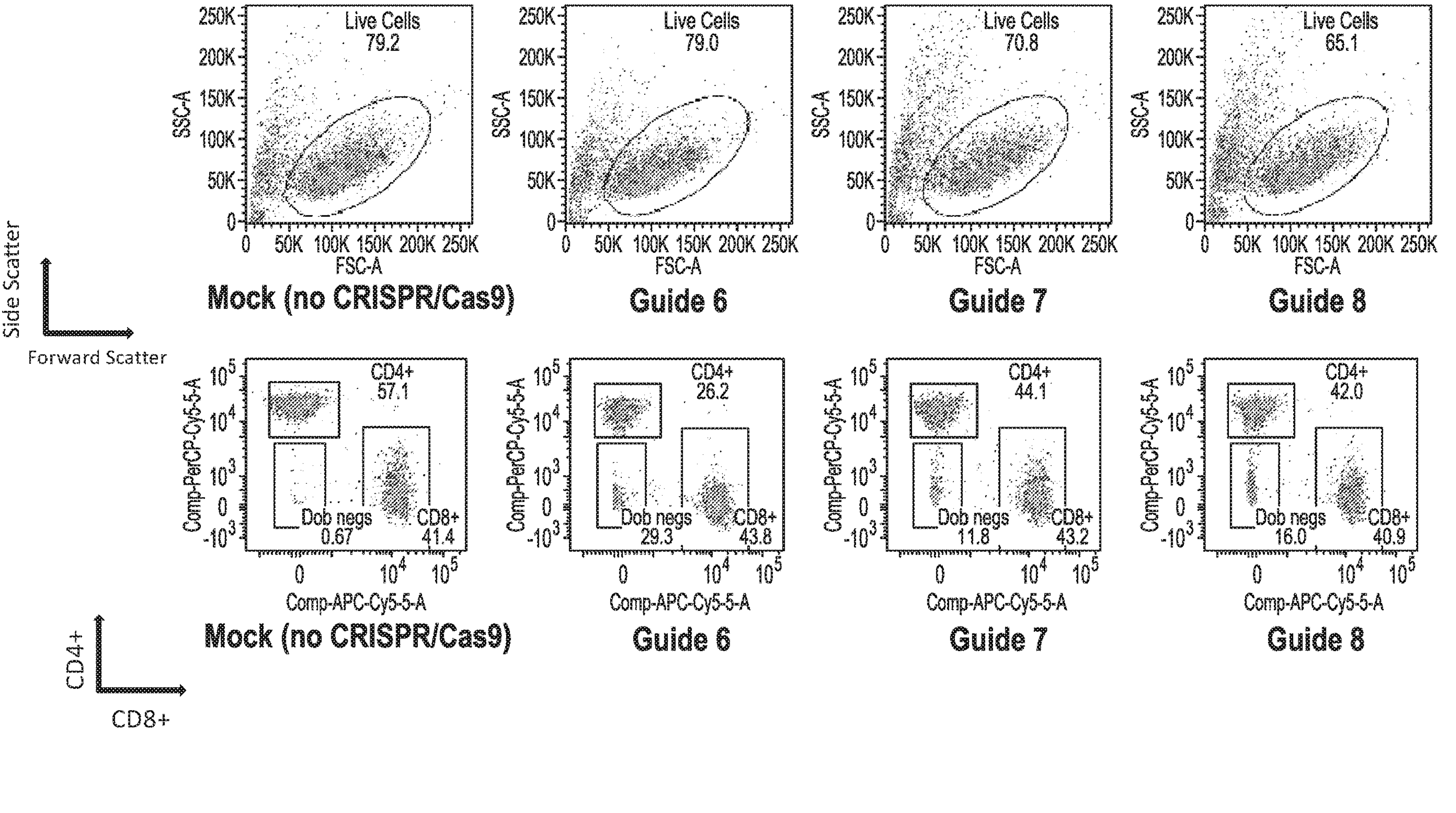
FIG. 2B depicts flow cytometry data with CD4+ cell line stained for CD8 on the X-axis plotted against CD4 on the Y-axis (lower row), in which cells were untreated (mock), or treated with Cas9 and a CRISPR guide polynucleotide (G6, G7, or G8).

Two further guides were also tested. FIG. 2B depicts flow cytometry data with CD4+ cell line stained for CD8 on the X-axis plotted against CD4 on the Y-axis (lower row), in which cells were untreated (mock), or treated with Cas9 and a CRISPR guide polynucleotide (G6, G7, or G8). G6 outperformed G7 and G8. For G6 treated cells, the percentage of CD4+ cells was lowest compared to the G7 or G8 treated cells; and the percentage of double negative CD4− and CD8− cells was higher with G6 treated cells compared to G7 or G8 treated cells.

Figure 3:
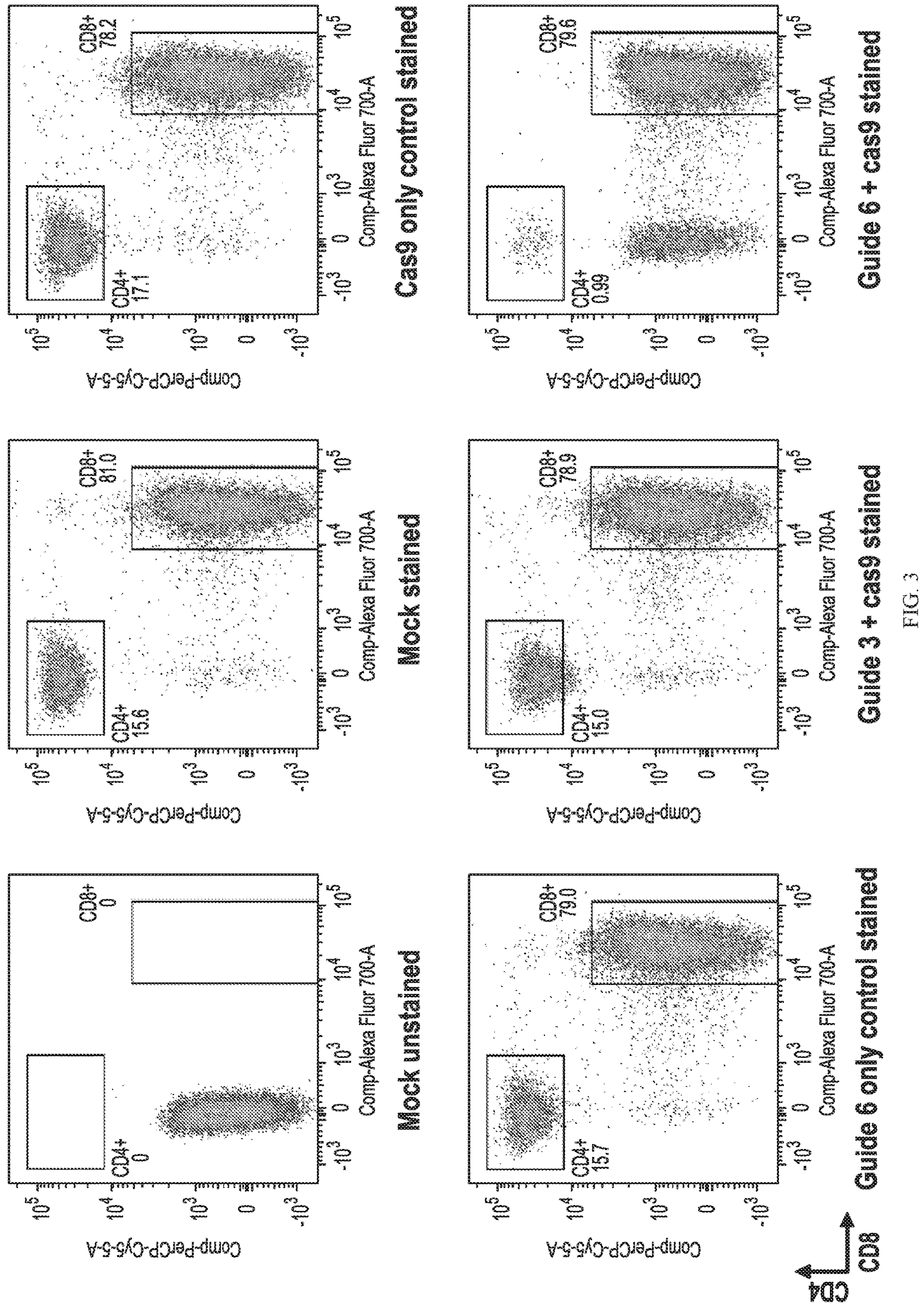
FIG. 3 depicts flow cytometry data from human primary T cells stained for CD4 and CD8 in which cells were untreated (mock), treated with Cas9 only, treated with CRISPR guide polynucleotide 6 only, or treated with Cas9 and either a CRISPR guide polynucleotide G3 or G6.

CD3+ cells were isolated from primary human peripheral blood mononucleated cells (PBMC). Guides were introduced as a RNP via electroporation. Data was generated at day 11 post Cas9+guide transfection, and cells were stained with CD4 and CD8. Controls included: untransfected and unstained cells; mock transfected cells stained for CD4 and CD8; cells transfected with Cas9 but no guide, stained for CD4 and CD8; and cells transfected with Guide 6 but no Cas 9, stained for CD4 and CD8 (FIG. 3). Test cells were treated with CRISPR/Cas9 and either Guide 3 or Guide 6 (FIG. 3). About 15.6% of mock transfected cells were CD4+ versus about 0.99% of the cells transfected with Guide 6. Thus, Guide 6 reduced cell surface expression of CD4 by about 94%. About 15.6% of mock transfected cells were CD4+ versus 15.0% of the cells transfected with Guide 3. Thus, Guide 3 reduced cell surface expression of CD4 by about 4%. In primary cells, Guide 6 outperformed Guide 3.

Figure 4A:
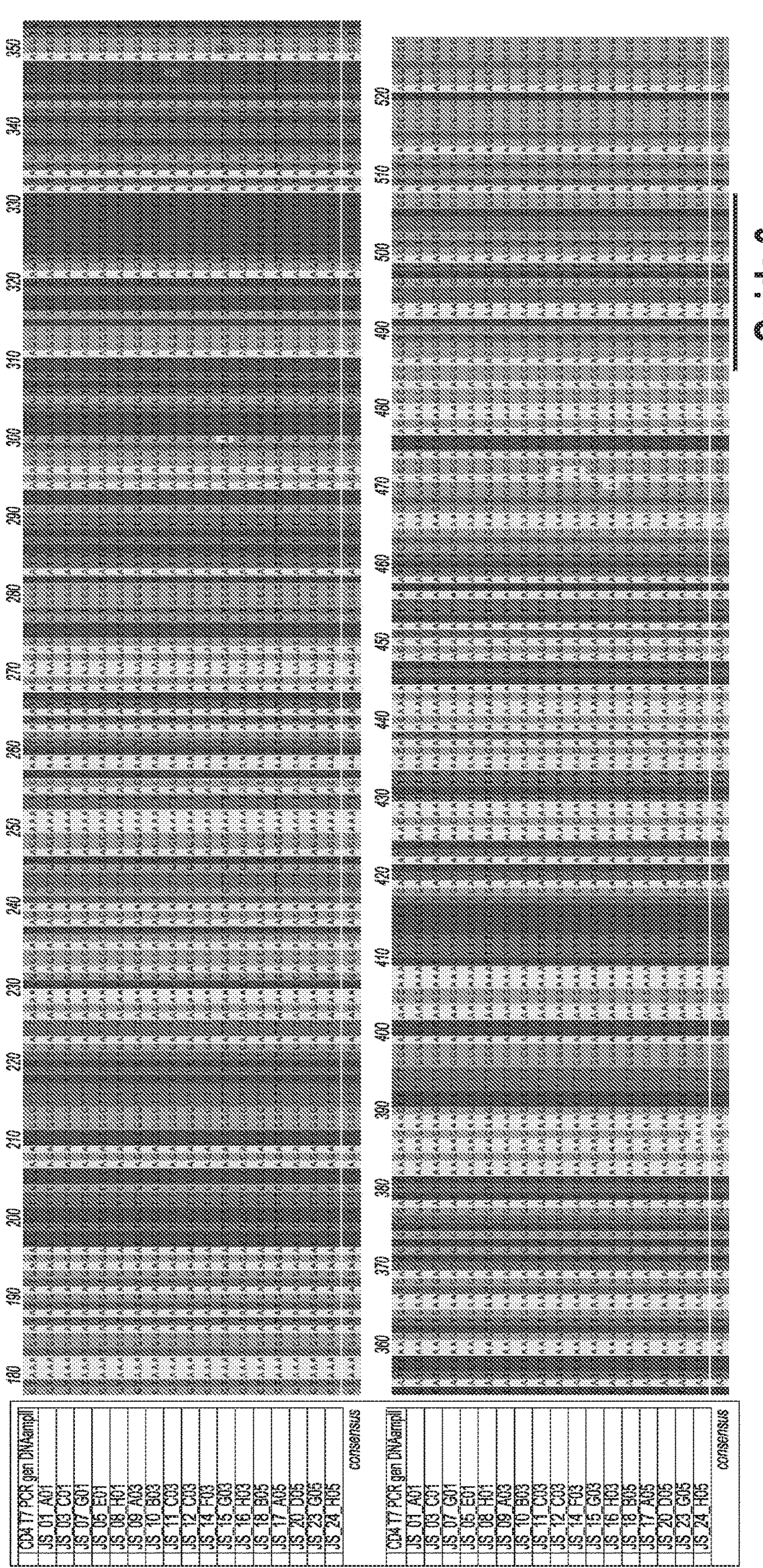
FIG. 4A depicts a comparison of genomic CD4 sequences obtained from 17 untreated control clones, with a consensus sequence shown in the bottom row of the top panel and the lower panel, and the G6 sequence is indicated below the sequences on the lower panel.
Figure 4B:
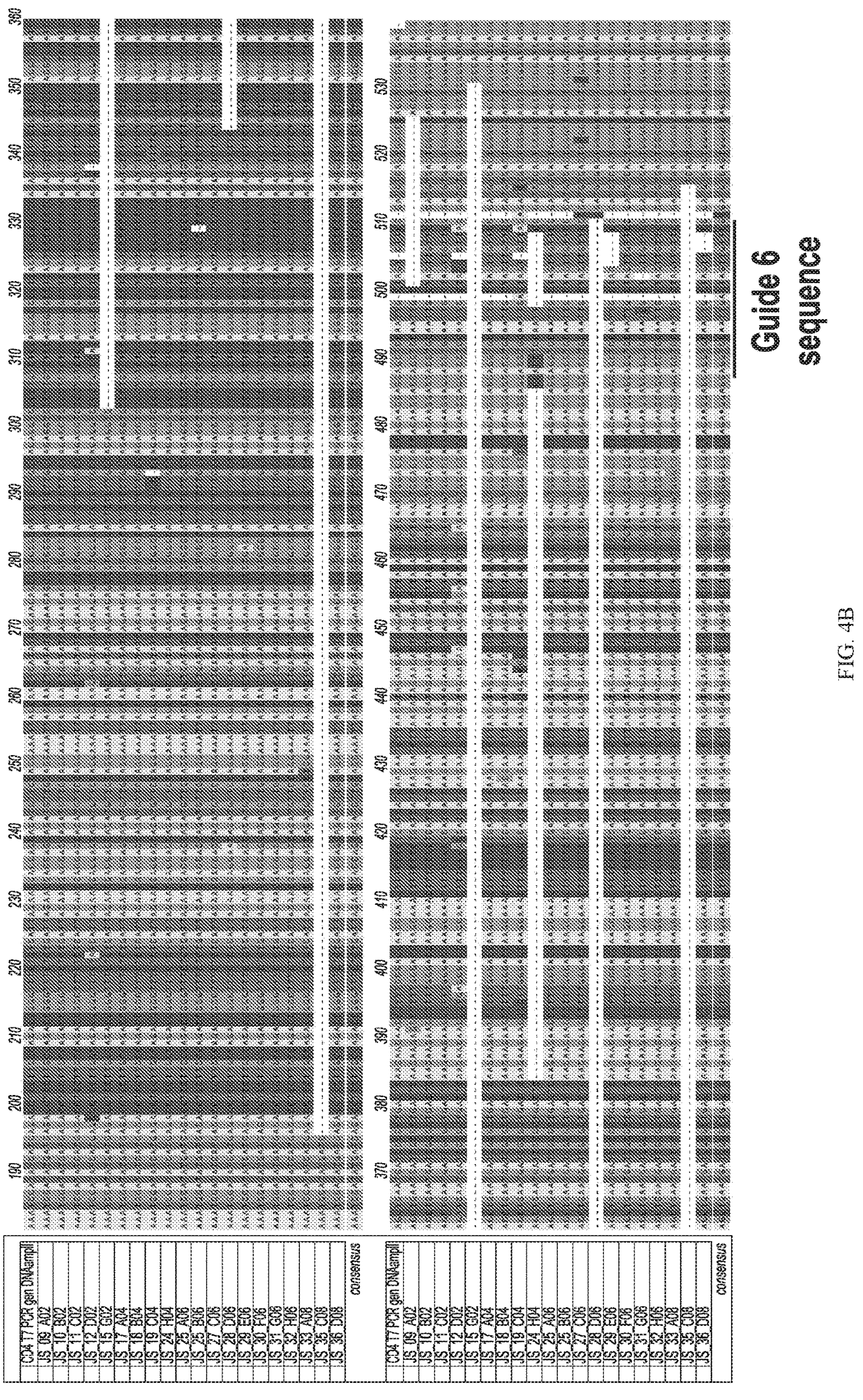
FIG. 4B depicts a comparison of genomic CD4 sequences obtained from 20 clones that had been treated with Cas9 and the G6 CRISPR guide polynucleotide, with the G6 inserted sequence indicated.

To confirm CD4 disruption at the genetic level, CD4 colony sequencing was performed on mock transfected (FIG. 4A) and Guide 6 transfected (FIG. 4B) primary cells. A region of the CD4 gene was sequenced from 17 untreated control clones, and 20 clones that had been treated with Cas9 and RNP with G6. In FIG. 4A and FIG. 4B, a consensus sequence is shown at the bottom row of each upper and lower panels, and the location of the 20 base pair Guide 6 CRISPR site is indicated below the consensus sequence. All 20 treated clones had insertions, deletions, or mutations at the Guide 6 CRISPR site.

Example 2—Preparation and Activity of Anti-CD4 CAR T Cells

This example relates to the activity of primary CD3+ T cells that include a disrupted CD4 gene and contain an anti-CD4 CAR, to deplete a targeted population of CD4+ cells. Primary CD3+ T cells were isolated, transfected with an anti-CD4 CRISPR RNP (Guide 6), and then transduced with an anti-CD4 chimeric antigen receptor (CAR) containing a blue fluorescent protein (BFP) reporter. The anti-CD4 CAR included a scFv having the amino acid sequence of SEQ ID NO:09:

(DIVMTQSPSSLAVSVGEKVTMICKSSQSLLYSTNQKNYLAWYQQKP
GQSPKLLIYWASTRESGVPDRFTGSGSGTDFTLTISSVKAEDLAVYY
CQQYYSYRTFGGGTKLEIKGGGGSGGGGSGGGGSEVKLQESGPELVK
PGASVKMSCKASGYTFTSYVIHWVRQKPGQGLDWIGYINPYNDGTDY
DEKFKGKATLTSDKSSSTAYMELSSLTSEDSAVYYCAREKDNYATGA
WFAYWGQGTTVTVSS)

The cells were grown for one week in vitro and then evaluated by flow cytometry, staining for CD4, CD8, and CAR (BFP) expression.

Figures 5A, 5B, 5C, 5D, 5E:
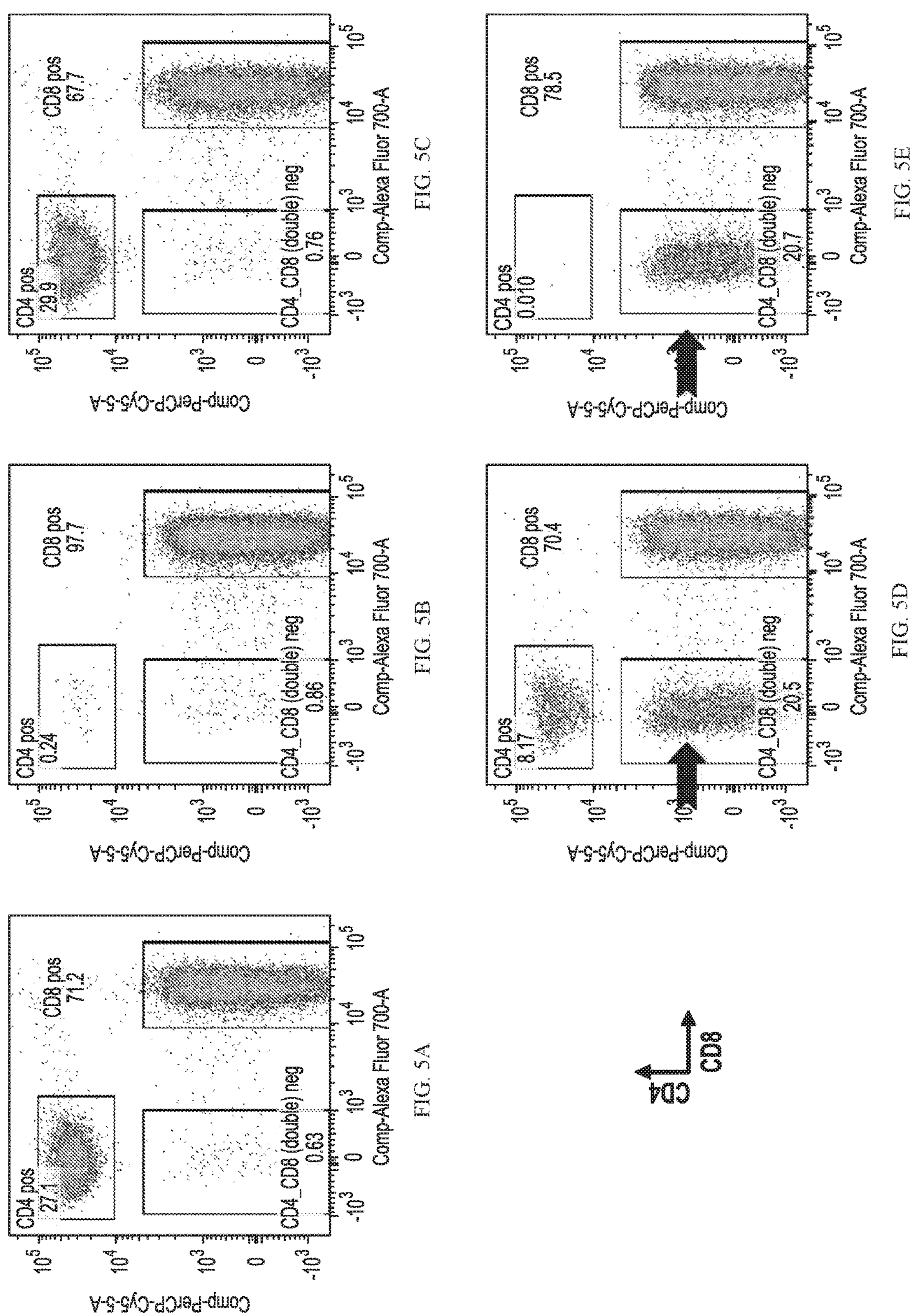
FIG. 5A depicts control flow cytometry data from primary CD3+ cells stained for CD4 and CD8 in which cells were untreated.
FIG. 5B depicts control flow cytometry data from primary CD3+ cells stained for CD4 and CD8 in which cells were transduced with a lentivirus containing a polynucleotide encoding an anti-CD4 CAR only.
FIG. 5C depicts control flow cytometry data from primary CD3+ cells stained for CD4 and CD8 in which cells were treated with the G6 CRISPR guide polynucleotide only.
FIG. 5D depicts flow cytometry data from primary CD3+ cells stained for CD4 and CD8 in which cells were treated with Cas9 and the G6 CRISPR guide polynucleotide.
FIG. 5E depicts flow cytometry data from primary CD3+ cells stained for CD4 and CD8 in which cells were treated with Cas9 and the G6 CRISPR guide polynucleotide and also transduced with a lentivirus containing a polynucleotide encoding an anti-CD4 CAR.

As shown in FIG. 5B, transduction with the anti-CD4 CAR efficiently depleted CD4-positive cells (reduction in CD4+ percentage from 27.1 to 0.24%). As shown in FIG. 5D, transfection with anti-CD4 CRISPR/Cas9 RNP depletes CD4-positive cells (reduction in CD4+ percentage from 27.1 to 8.17%). As shown in FIG. 5E, transduction with the anti-CD4 CAR in combination with transfection with anti-CD4 CRISPR/Cas9 RNP profoundly depleted CD4+ cells (27.1 to 0.01%) and resulted in the emergence of a CD4 and CD8 double negative population (0.63 to 20.7%). Thus, compared to controls, anti-CD4 CAR T cells without CD4 disruption depleted nearly all CD4+ cells; and that cells with a disrupted CD4 gene but without the anti-CD4 CAR substantially decreased the level of CD4+ cells. However, using a combination of the cells treated with anti-CD4 CRISPR and containing the anti-CD4 CAR, a profound depletion of CD4+ T cells was observed, and a clear population of double negative (CD4 and CD8 negative), CAR(BFP)+ cells emerged.

Figures 6A, 6B, 6C, 6D, 6E:
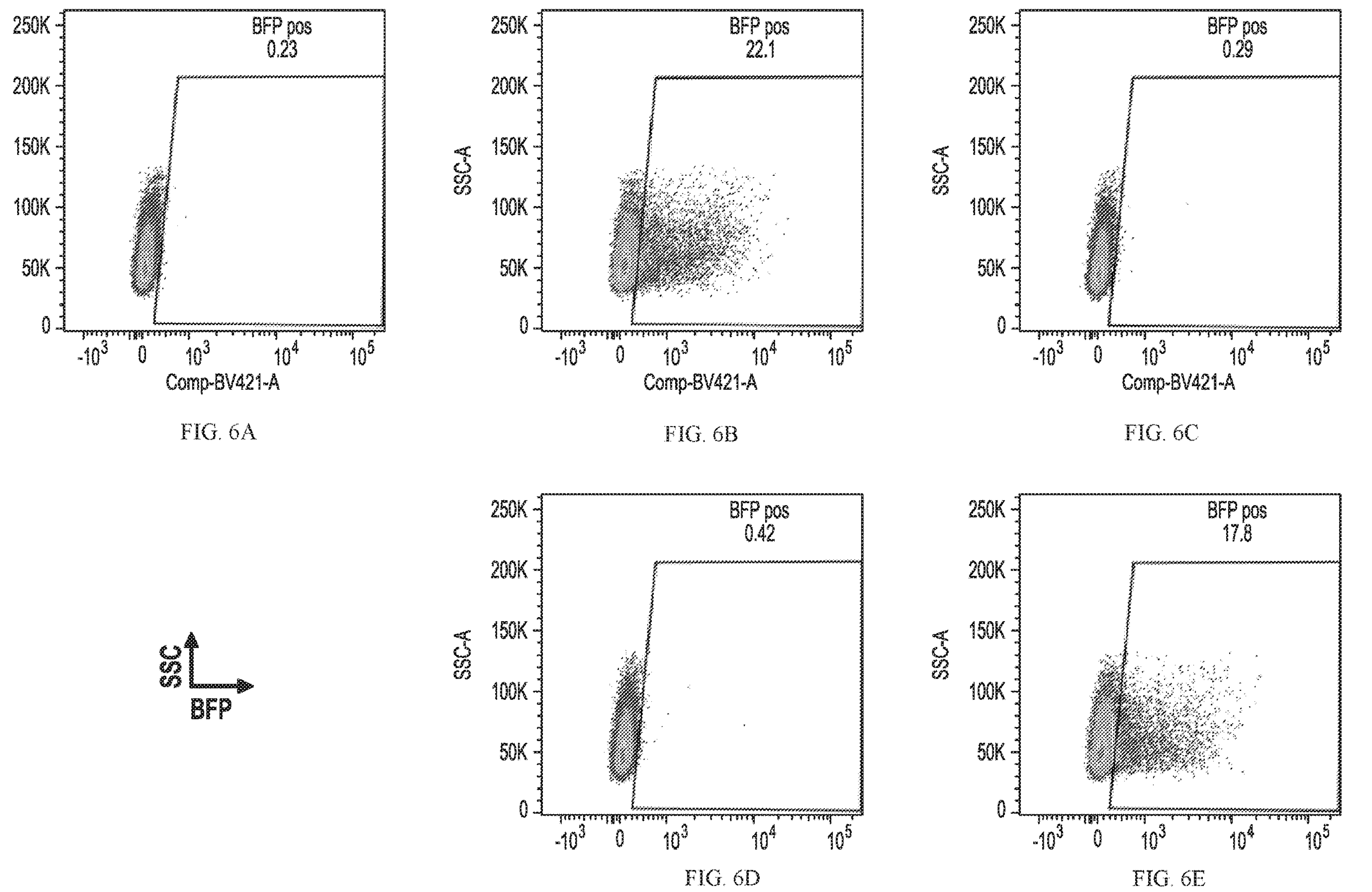
FIG. 6A depicts control flow cytometry data from primary CD3+ cells which were untreated.
FIG. 6B depicts control flow cytometry data from primary CD3+ cells which were transduced with a lentiviral vector containing a polynucleotide encoding an anti-CD4 CAR only, which expresses blue fluorescent protein.
FIG. 6C depicts control flow cytometry data from primary CD3+ cells which were treated with the G6 CRISPR guide polynucleotide only.
FIG. 6D depicts flow cytometry data from primary CD3+ cells which were treated with Cas9 and the G6 CRISPR guide polynucleotide.
FIG. 6E depicts flow cytometry data from primary CD3+ cells which were treated with Cas9 and the G6 CRISPR guide polynucleotide and also transduced with a lentiviral vector containing a polynucleotide encoding an anti-CD4 CAR, which expresses blue fluorescent protein. All plots in FIG. 6 show blue fluorescent protein (BFP) on the X-axis versus side scatter area (SSC-A) on the Y-axis.
Figure 7A:
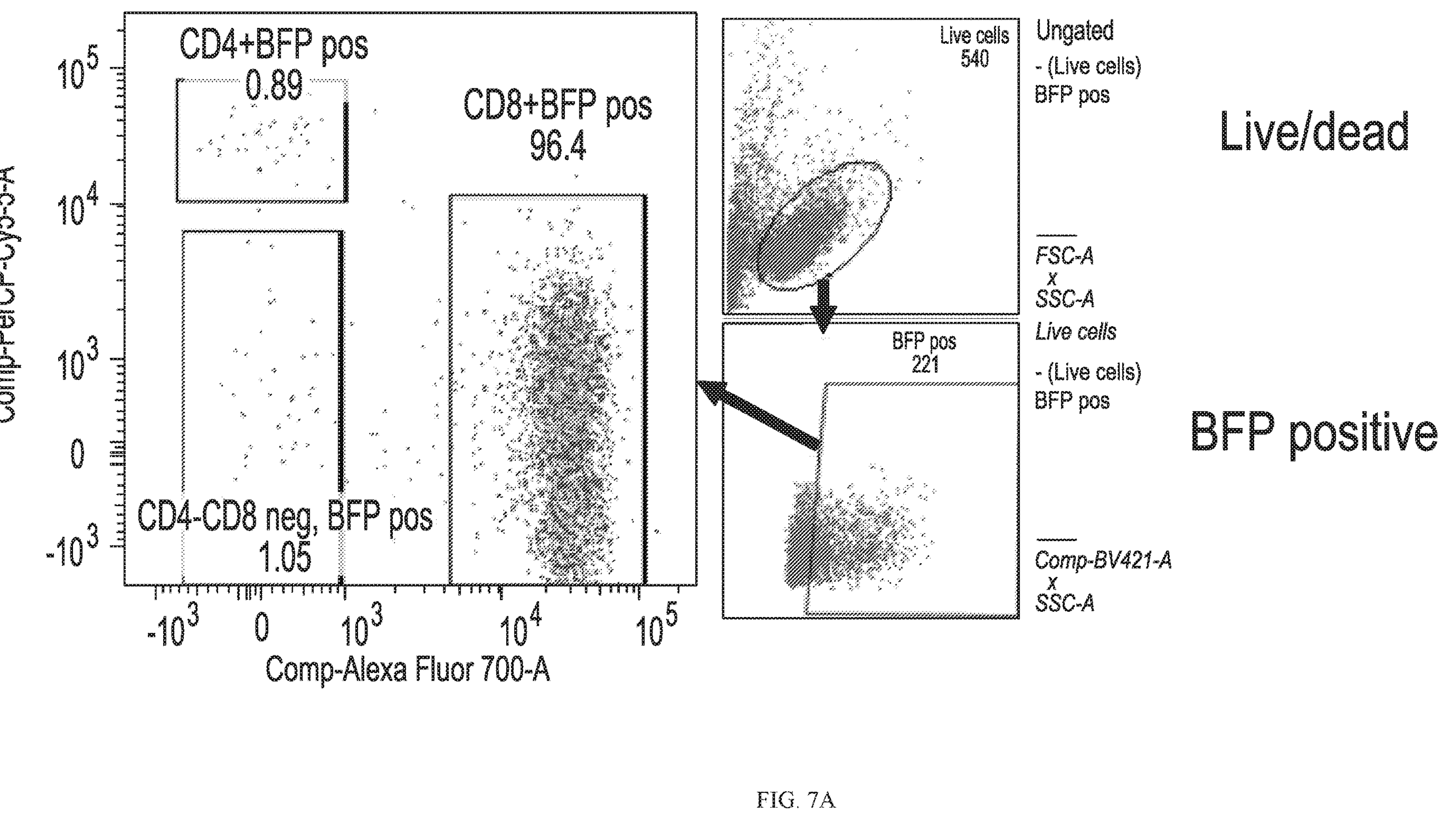
FIG. 7A depicts a back-gating analysis of BFP (expressed from the CAR) positive cells with flow cytometry data from primary CD3+ cells stained for CD4 and CD8 in which cells were transduced with a lentiviral vector containing a polynucleotide encoding an anti-CD4 CAR only.
Figure 7B:
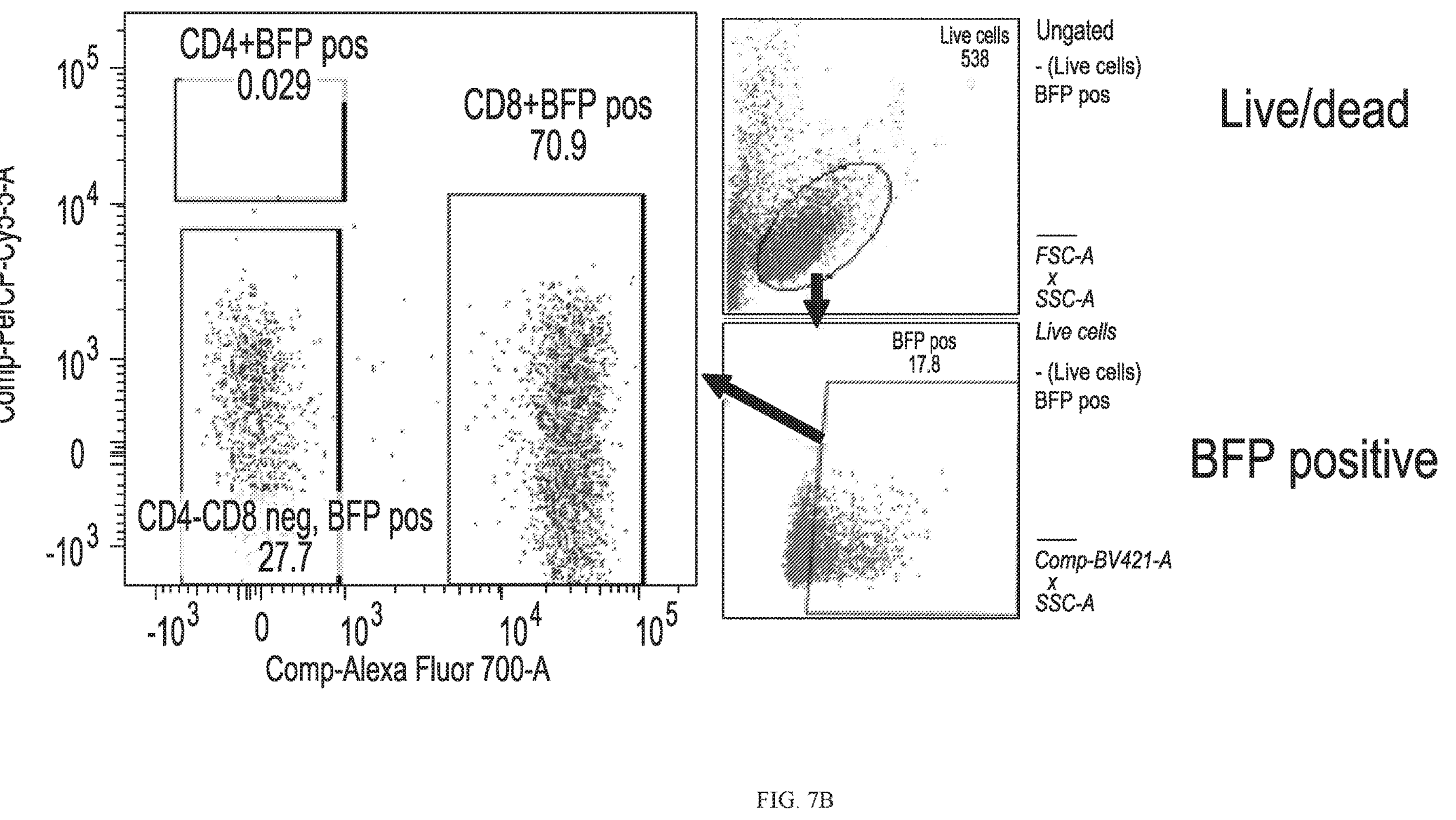
FIG. 7B depicts a back-gating analysis of BFP (expressed from CAR) positive cells with flow cytometry data from primary CD3+ cells stained for CD4 and CD8 in which cells were treated with Cas9 and the G6 CRISPR guide polynucleotide, and also transduced with a lentiviral vector containing a polynucleotide encoding an anti-CD4 CAR.

Cells were treated with anti-CD4 CRISPR/Cas 9 RNP (Guide 6) and transduced with an anti-CD4 CAR that contained blue fluorescent protein (BFP). Cells were evaluated for BFP expression by flow cytometry. As shown in FIG. 6B, and FIG. 6E, BFP expression was substantially restricted to the cells transduced with BFP-containing CAR. As shown in FIG. 7A and FIG. 7B, cells were stained with CD4 (Y-axis) and CD8 (X-axis) staining after gating on live CAR (BFP+) cells. Because CAR expression was modest (17.8%), back-gating on BFP+ cells further demonstrated that specifically among the anti-CD4 CRISPR treated anti-CD4 CAR T cells that the CD4+ cells were depleted (0.029%) and that a population of CD4− and CD8− double negative cells emerged (27.7%).

Example 3—Functional Analysis of CAR T Cells with Disrupted CD4

This example relates to the activity of primary CD3+ T cells that included a disrupted CD4 gene and contained an anti-CD19 CAR, as measured by intracellular cytokine expression. CD4 disruption might be expected to render CD4+ lymphocytes non-functional. Thus, the function of CAR T cells that were engineered to not express CD4 was investigated.

Figure 8:
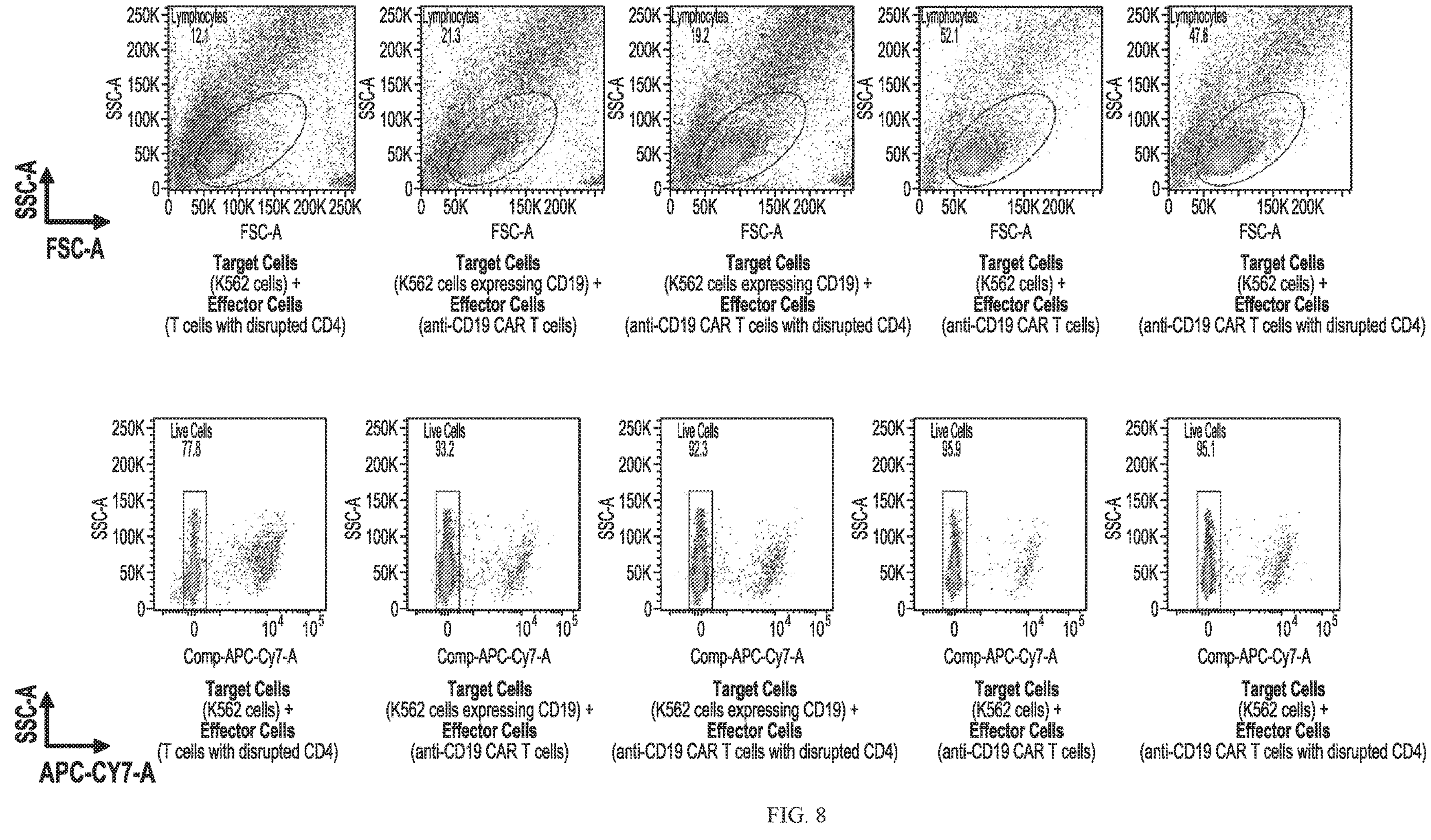
FIG. 8 shows functional data depicted by flow cytometry data after T cells or CAR T cells are mixed with target cells. The target cells are K562 cells that were or were not transduced with a lentiviral vector contain a polynucleotide encoding CD19. The effector cells were T cells that were or were not transduced with a lentiviral vector containing a polynucleotide encoding an anti-CD19 CAR and were or were not transfected with the G6 CRISPR guide polynucleotide and Cas9.

Appropriate cytokine expression (TNF-α, IL-2, and IFN-g) was evaluated in the CAR T cells when in contact with cells expressing target antigen as a measure of CAR T cell function. Anti-CD19 CAR T cells with and without CD4 disruption were prepared and mixed with targets cells (K562 cells or K562 cells engineered to express CD19) at a 2:1 Effector:Target ratio. BFP was expressed by the anti-CD19 CAR construct. After six hours, cells were evaluated by intracellular cytokine expression using flow cytometry. FIG. 8 shows flow cytometry data after the anti-CD19 CAR T cells with and without CD4 disruption are mixed with target cells which do or do not express CD19. Cells were evaluated for lymphocyte morphology (FIG. 8, top row), and live dead staining (FIG. 8, bottom row).

Figure 9:
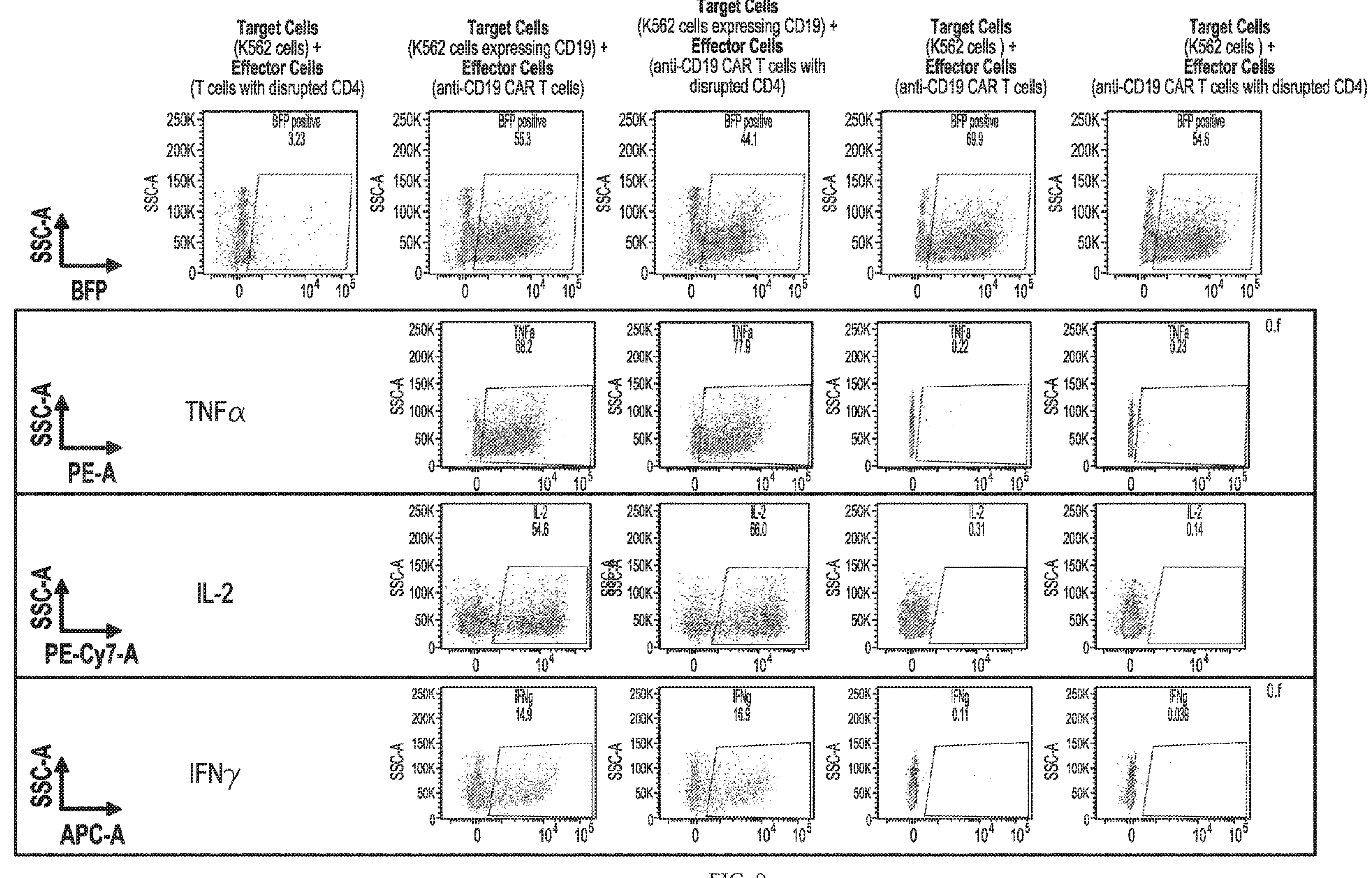
FIG. 9 shows functional data depicted by flow cytometry data after T cells or CAR T cells are mixed with target cells. The target cells are K562 cells that were or were not transduced with a lentiviral vector containing a polynucleotide encoding CD19. The effector cells were T cells that were or were not transduced with a lentiviral vector containing a polynucleotide encoding an anti-CD19 CAR and were or were not transfected with the G6 CRISPR guide polynucleotide and Cas9.

Cytokine expression (TNF alpha, IL-2, and IFN gamma) was evaluated in BFP+ CAR T-cells. Anti-CD19 CAR T-cells only expressed cytokines in the presence of CD19-expressing target cells (FIG. 9). Negative controls did not produce significant amounts of cytokine. Wildtype CAR T-cells and CAR T-cells with CD4 disruption produced similar amounts of cytokine. Thus, CART cells with and without CD4 disruption had similar function, as evaluated by comparing the percentage of cells that express cytokine. Unexpectedly, for TNF alpha and IL-2 the percentage of cells that expressed cytokine was higher in the CD4 disrupted in the CAR T cells, suggesting that there may be an inherent benefit to disrupting CD4 in CAR T cells. This was not anticipated a priori.

Figure 10:
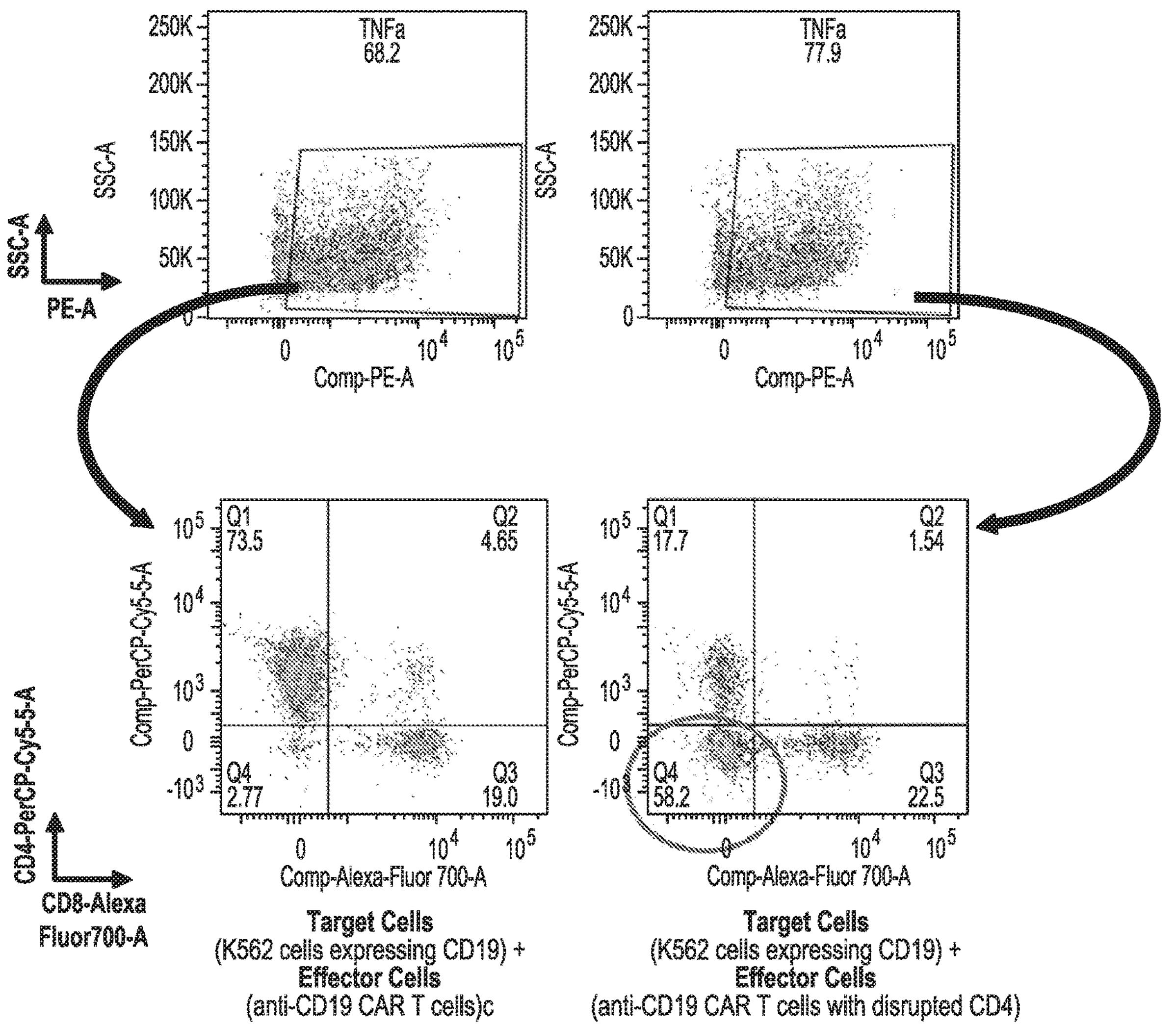
FIG. 10 depicts flow cytometry data relating to TNF-α expression for target K562 cells expressing CD19 when mixed with effector cells including T cells containing an anti-CD19 CAR (left panels), or T cells with disrupted CD4 and containing an anti-CD19 CAR (right panels), and stained for SCC-A and PE-A (upper panels), or CD4-PerCPCy5.5-A and CD8-Alexa Fluor 700 A (lower panels). Among the TNF-α-expressing, live, CAR+(BFP+) lymphocytes, an increased population of CD4 and CD8 double negative population is identified when CD4 is disrupted, circled population in lower right panel.
Figure 11:
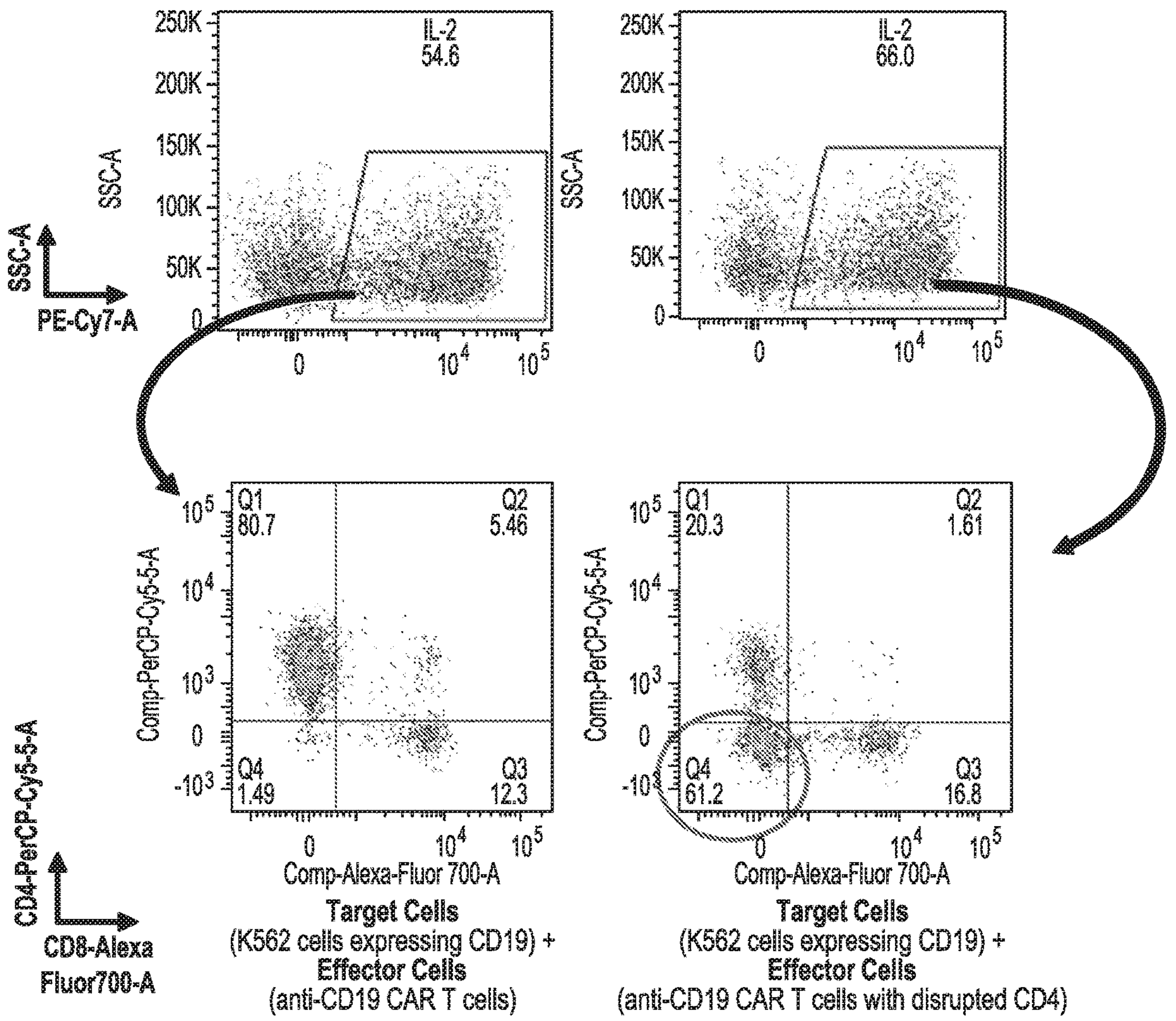
FIG. 11 depicts flow cytometry data relating to IL-2 expression for target K562 cells expressing CD19 when mixed with effector cells including T cells containing an anti-CD19 CAR (left panels), or T cells with disrupted CD4 and containing an anti-CD19 CAR (right panels), and stained for SCC-A and PE-Cy7-A (upper panels), or CD4-PerCPCy5.5-A and CD8-Alexa Fluor 700 A (lower panels). Among the IL-2-expressing, live, CAR+(BFP+) lymphocytes, an increased population of CD4 and CD8 double negative population is identified when CD4 is disrupted, circled population in lower right panel.
Figure 12:
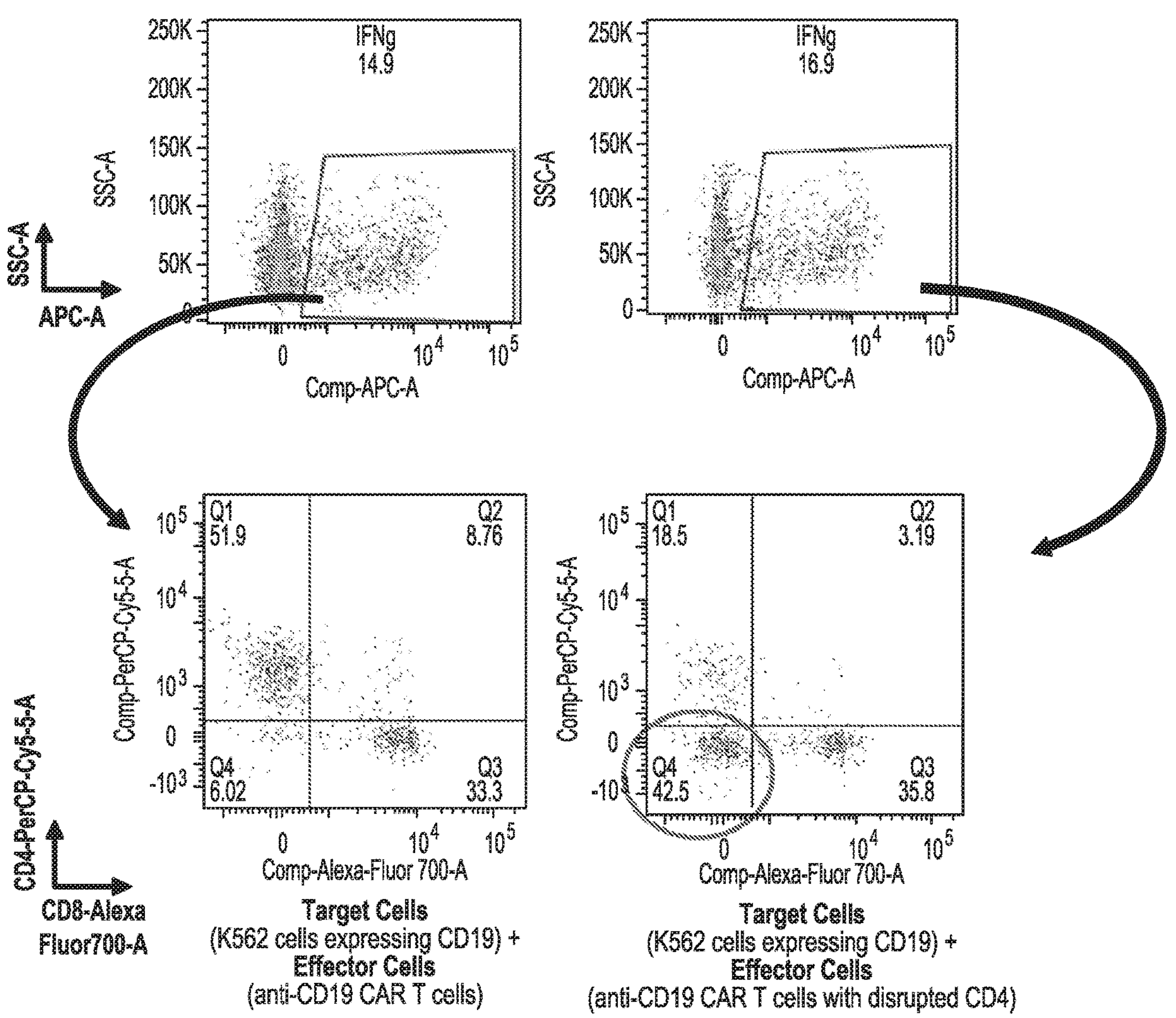
FIG. 12 depicts flow cytometry data relating to IFN-gamma expression for target K562 cells expressing CD19 when mixed with effector cells including T cells containing an anti-CD19 CAR (left panels), or T cells with disrupted CD4 and containing an anti-CD19 CAR (right panels), and stained for SCC-A and APC-A (upper panels), or CD4-PerCPCy5.5-A and CD8-Alexa Fluor 700 A (lower panels). Among the IFN-gamma-expressing, live, CAR+(BFP+) lymphocytes, an increased population of CD4 and CD8 double negative population is identified when CD4 is disrupted, circled population in lower right panel.

Back-gating on the cytokine producing CAR T cells demonstrated that in the CD4-disrupted CAR T cells the cytokine was being produced by double negative cells (CD4 and CD8 negative). The phenotype of TNFα producing CAR T-cells was investigated. As shown in FIG. 10, without CD4 disruption the majority of the TNFα producing cells were CD4+. After CD4 disruption the majority of TNFα producing cells were CD4/CD8 double negative. The phenotype of IL-2 producing CAR T-cells was investigated. As shown in FIG. 11, without CD4 disruption the majority of the IL-2 producing cells were CD4+, and after CD4 disruption the majority of IL-2 producing cells were CD4/CD8 double negative. The phenotype of IFN gamma producing CAR T-cells was investigated. As shown in FIG. 12, without CD4 disruption the majority of the IFN gamma producing cells were CD4+, and after CD4 disruption the majority of IFN gamma producing cells were CD4/CD8 double negative.

Figure 13:
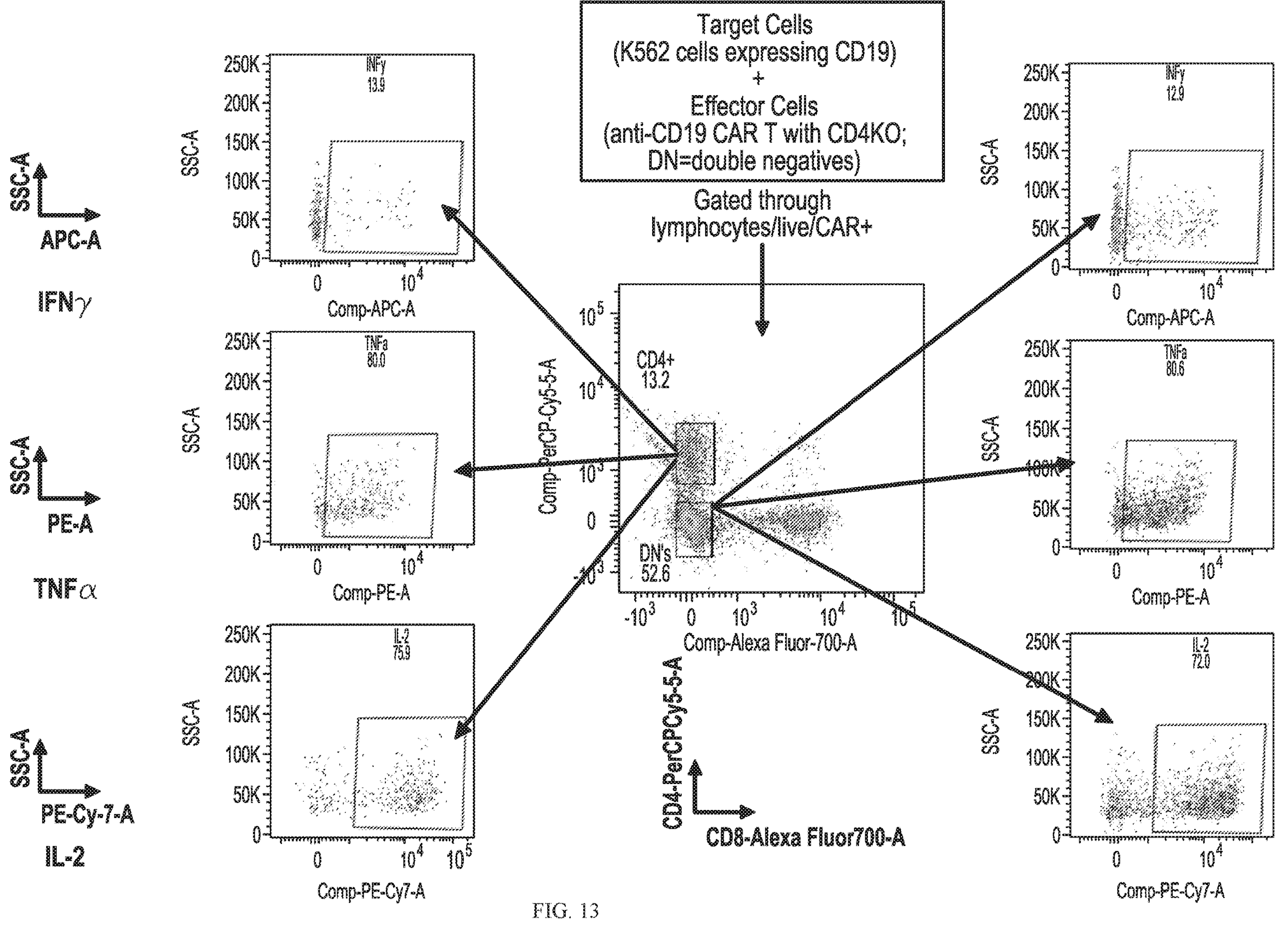
FIG. 13 depicts flow cytometry data in which target K562 cells expressing CD19 mixed with effector cells including T cells with disrupted CD4 and containing an anti-CD19 CAR, and gated through lymphocytes/live/CAR+, and stained to detect expression of TNF-α, IL-2, and IFN-gamma. The panels of the left represent the cytokine expression in the CD4+ CAR T cells. The panels on the right represent the cytokine expression in the CAR T cells engineered not to express CD4.

Cytokine production by CD4-positive and CD4-negative anti-CD19 CAR T-cells within a single cell sample in which CD4 was disrupted was compared. As shown in FIG. 13, CD4-disruption was not 100% efficient, so there was a mixture of CD4+ and CD4-CAR T cells; the residual CD4+ CAR T cells produced similar amounts of cytokine as the CD4-disrupted CAR T cells.

Figure 14:
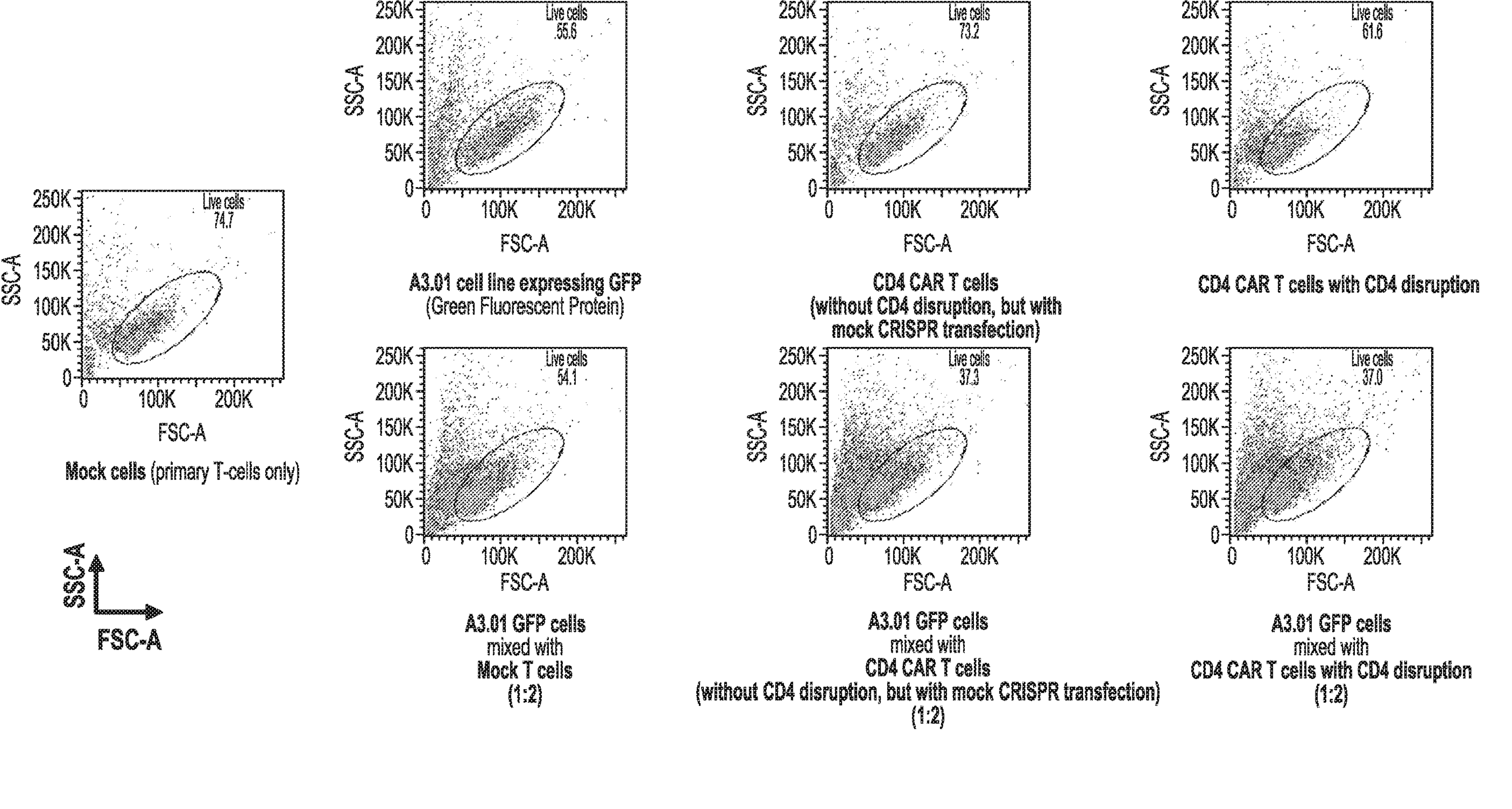
FIG. 14 depicts flow cytometry data showing the morphology (forward scatter on the X-axis versus side scatter on the Y-axis) of a different target and effector cell combinations. The target cells are a CD4+ cell line (A3.01 cells) transduced with a lentiviral vector containing a polynucleotide encoding green fluorescent protein (GFP). The effector cells are T cells, that are either transduced with a lentiviral vector containing a polynucleotide encoding an anti-CD4 CAR, and/or transfected with Cas9 and a polynucleotide encoding the G6 CRISPR guide targeting CD4. The target cells are mixed at a 2:1 ratio for 22 hours with effector cells.

Cell morphology of anti-CD4 CART cells was compared between with and without CD4 disruption when they are mixed with a GFP+CD4+ cell line (A3.01 cells), assessed by flow cytometry. Mock and CAR T-cells with/without CD4 disruption were mixed with A3.01-GFP cells at a ratio at a 2:1 for 22 hours. As shown in FIG. 14, CD4 disrupted CAR T-cells mixed with a CD4+ cell line (A3.01) have similar morphology based on forward and side scatter.

Figure 15:
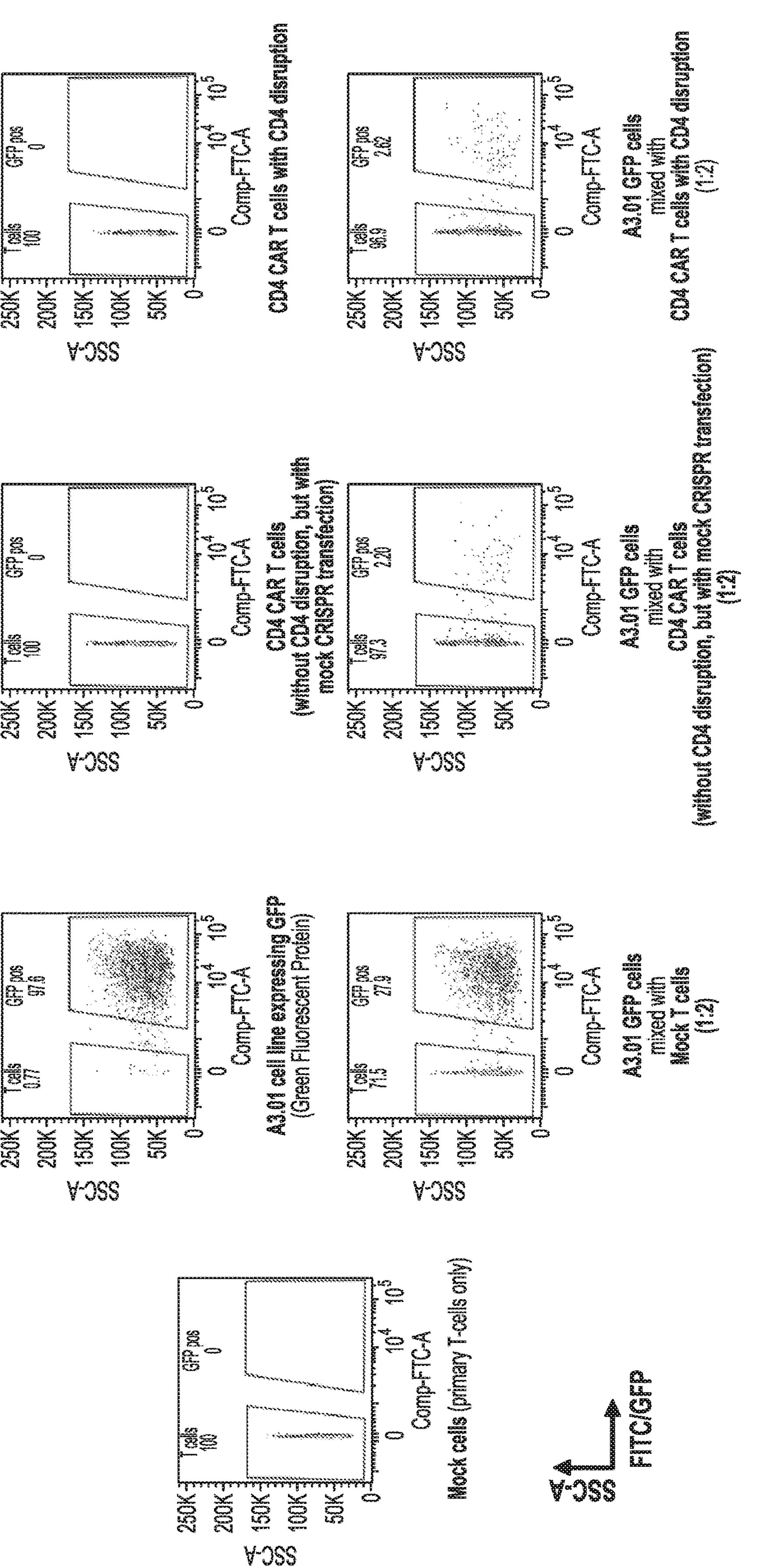
FIG. 15 depicts flow cytometry data showing the fate of the GFP-expressing CD4+ target cells under different conditions. The target cells are a CD4+ cell line (A3.01 cells) transduced with a lentiviral vector containing a polynucleotide encoding green fluorescent protein (GFP). The effector cells are T cells, that are either transduced with a lentiviral vector containing a polynucleotide encoding an anti-CD4 CAR, and/or transfected with Cas9 and a polynucleotide encoding the G6 CRISPR guide targeting CD4. The target cells are mixed at a 2:1 ratio for 22 hours with effector cells. The lower right panel show that most GFP-expressing CD4+ cells are depleted when mixed with the anti-CD4 CAR-expressing cells.

The activity of CART cells with disrupted CD4, was evaluated by assessing their ability to kill target cells. As shown in FIG. 15, anti-CD4 CAR T cells with or without CD4 disruption were equally effective at depleting the GFP+CD4+ cell line, as indicated by the lack of GFP/FITC+ cells in the lower right two panels, compared to the lower left panel. Thus, CAR T-cells with disrupted CD4 were functional and killed target cells with comparable efficiency to CD4+ CAR T-cells without CD4 disruption.

Example 4—CD4 Disruption Protects T Cells and CAR T Cells from HIV Infection

This example relates to the activity of T cells that include a disrupted CD4 gene via Cas9 and G6 treatment described above, and T cells that include a disrupted CD4 gene and contain an anti-CD19 CAR, co-cultured with HIV-infected cells. Cells were mixed with allogenic HIV-infected cells at a 2:1 ratio.

Figure 16:
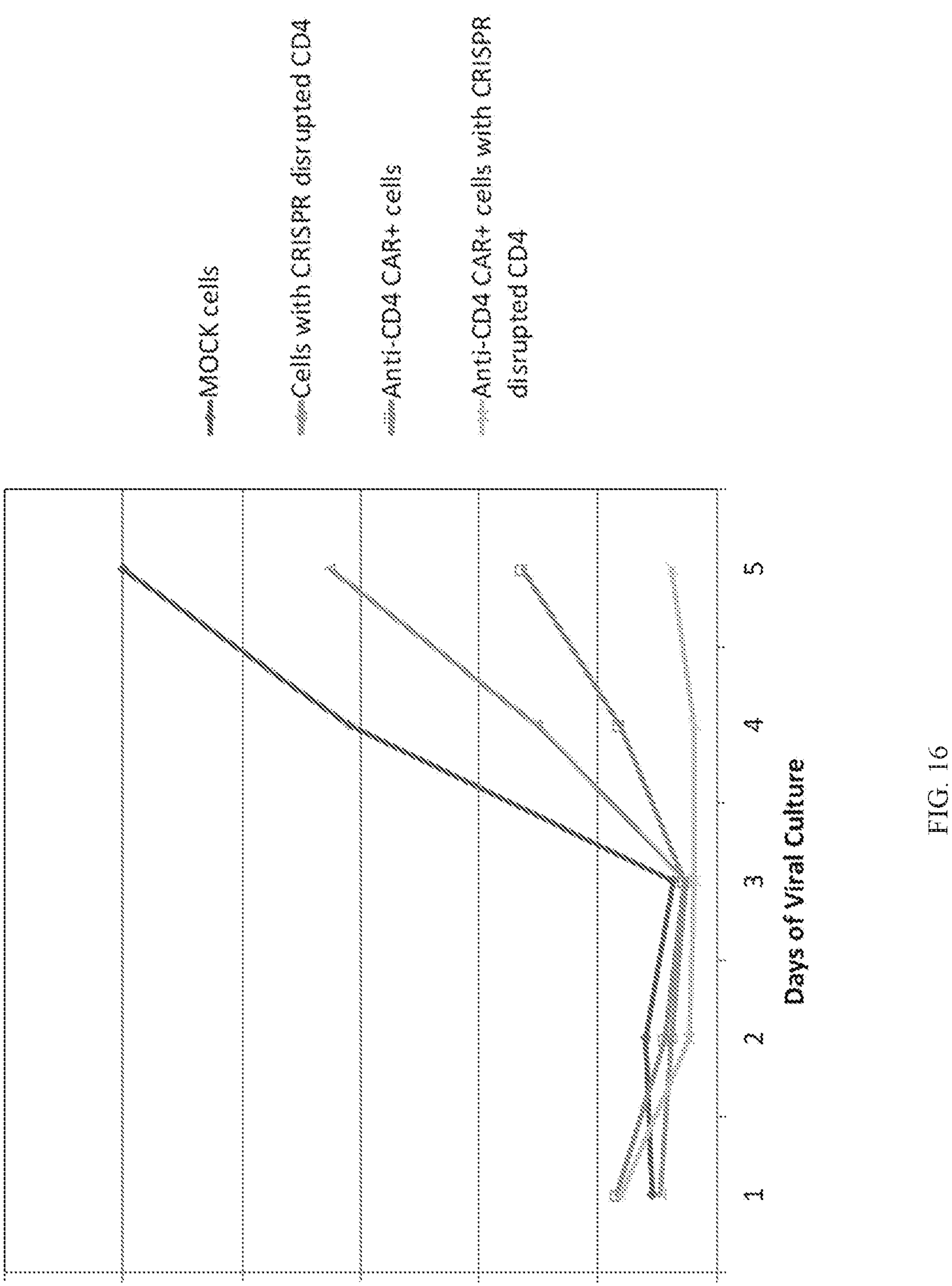
FIG. 16 depicts a graph of HIV p24 capsid concentration in viral culture over time 5 days in the presence of for various effector cells, including control cells (mock), cells with disrupted CD4, cells containing an anti-CD4 CAR, and cells with disrupted CD4 and containing an anti-CD4 CAR. Both the anti-CD4 CRISPR-treated effector cells and the anti-CD4 CAR-expressing cells reduce HIV protein, however the combination is more effective at reducing HIV than either approach alone.

Various T cells were prepared including control cells (mock), cells with disrupted CD4, cells containing an anti-CD4 CAR, and cells with disrupted CD4 and containing an anti-CD4 CAR. These engineered T cells were mixed with allogenic HIV-infected cells at a 2:1 ratio. The culture was monitored for HIV protein production for 5 days as measured by HIV capsid (p24) ELISA. As shown in FIG. 16, HIV replicated in HIV-infected cells mixed with mock effector T cells. However, in the presence of CD4-disrupted non-CAR T cells, less HIV protein was produced, which demonstrated that CD4-disruption reduced HIV replication. Anti-CD4 CAR T cells without CD4 disruption decreased HIV protein by more than 50%, demonstrating for the first time that that anti-CD4 CAR T cell therapy inhibits HIV replication. Anti-CD4 CAR T cells with CD4 disruption decreased viral production more than either non-CAR T cells with CD4 disruption or anti-CD4 CAR T cells without CD4 disruption alone, demonstrating the advantage of combining these strategies.

Figure 17:
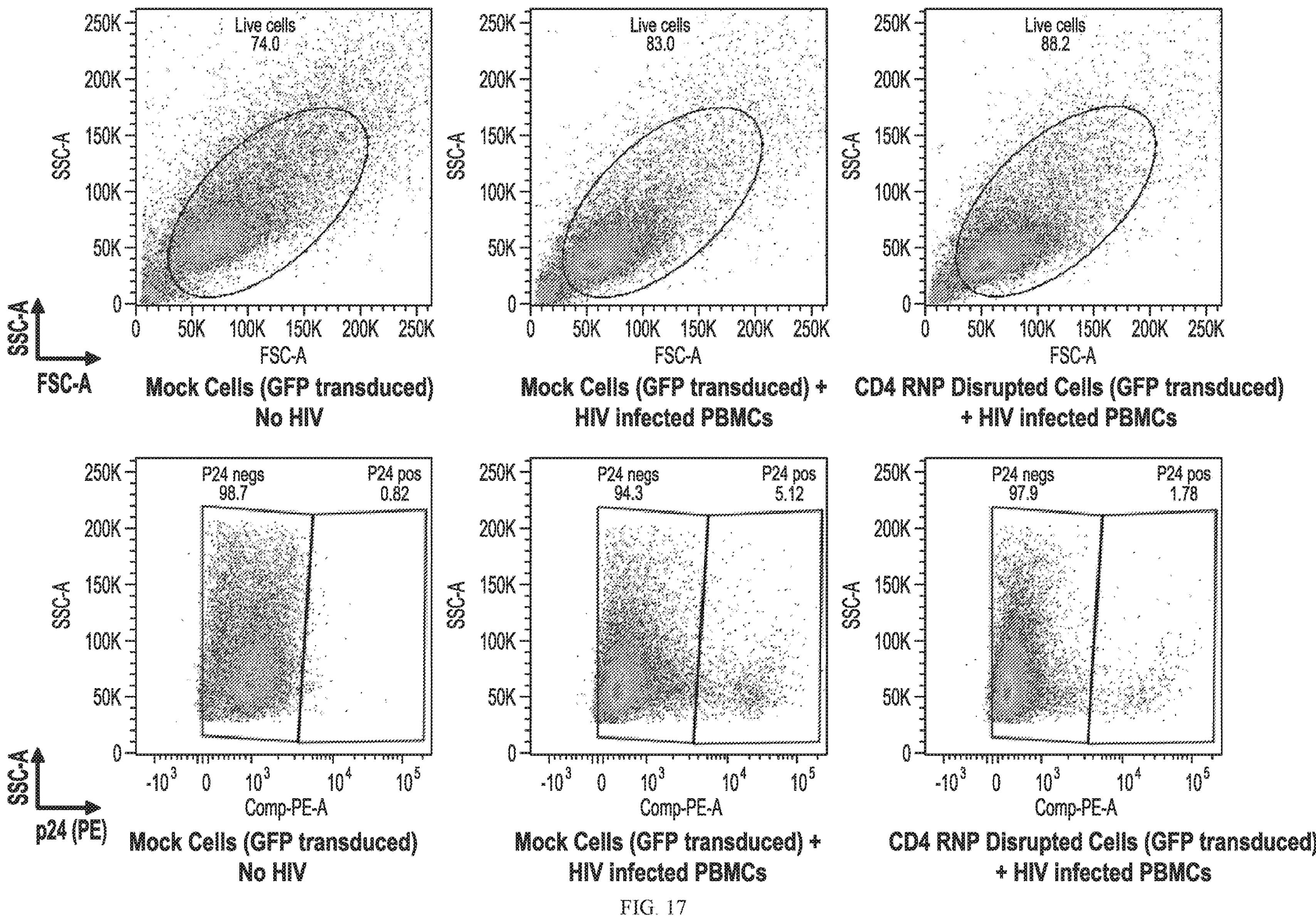
FIG. 17 depicts flow cytometry data in which target HIV infected peripheral blood mononucleated cells (PBMCs) were mixed with control cells (mock), or cells with disrupted CD4. A 65% reduction in percentage of HIV+ (p24+) cells was observed after CD4 disruption (5.12% versus 1.78% of cells infected, compare the two lower right panels).

CD4 disrupted and mock untreated cells were labelled with GFP via a GFP expressing lentiviral vector, and then mixed with allogenic HIV-infected peripheral blood mononucleated cells (PBMCs) at a 2:1 ratio. The percentage of HIV-infected cells was measured by intra-cellular staining for HIV capsid (p24) and assessed by flow cytometry after 2-3 days. In the absence of CD4 disruption, approximately 5.1% of all cells became HIV infected (FIG. 17, lower row, center panel). In contrast, when cells were exposed to an anti-CD4 CRISPR, only 1.8% of cells because HIV positive (FIG. 17, lower row, right panel). This was a 65% reduction in the percentage of HIV-infected cells and demonstrates that CD4-disruption reduces HIV infection in T cells.

Figure 18:
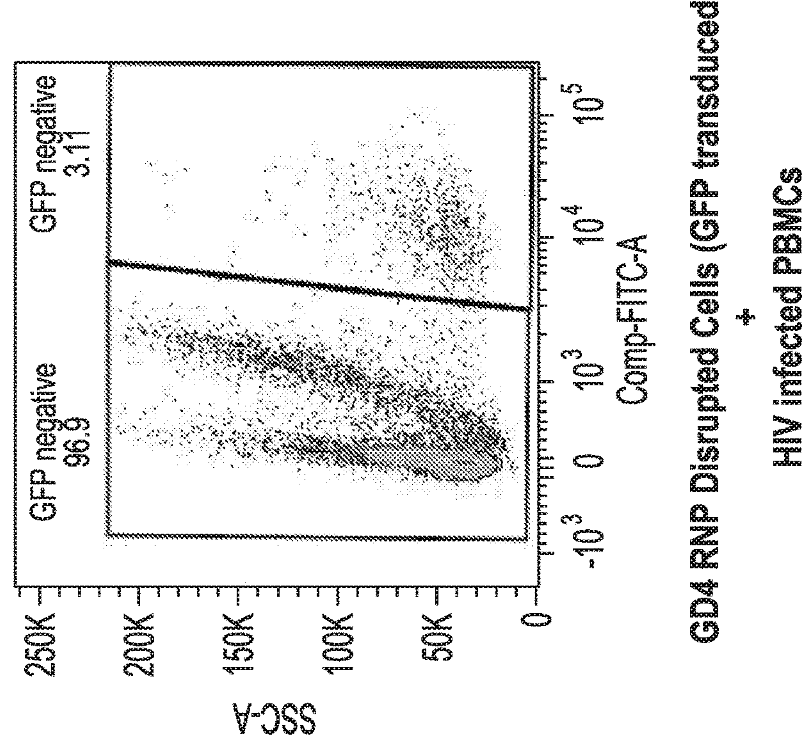
FIG. 18 depicts flow cytometry data in which HIV infected PBMCs were mixed with GFP+ control cells (mock), or GFP+ cells with disrupted CD4.
Figure 18:
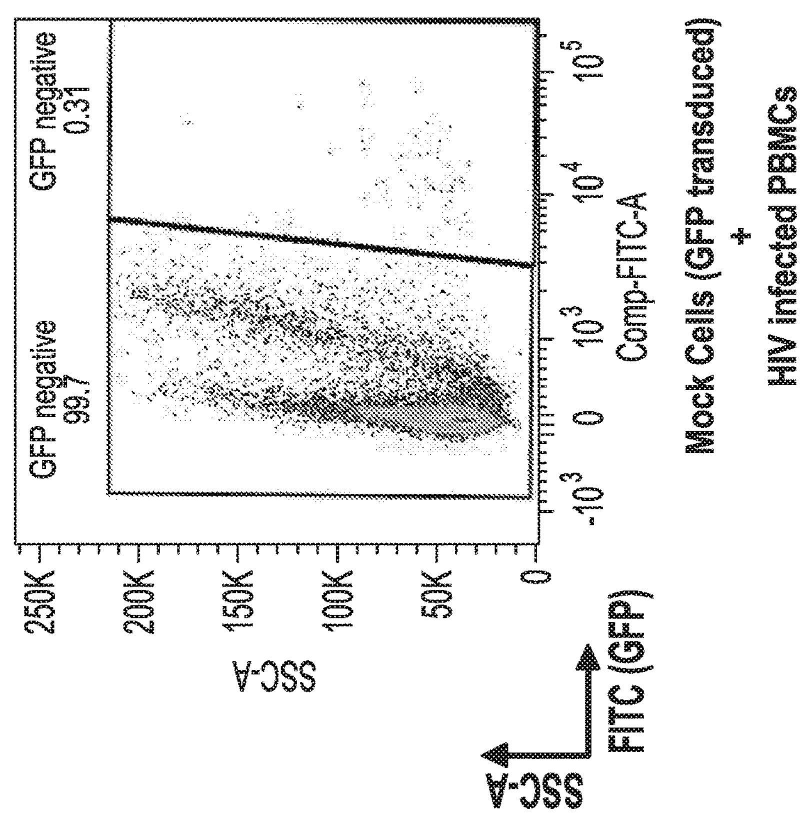

CD4 disrupted and mock untreated cells were labelled with GFP via a GFP expressing lentiviral vector, and then mixed with allogenic HIV-infected PBMC at a 2:1 ratio. After two days, cells were assessed for GFP expression by flow cytometry. As shown in FIG. 18 (left panel), in the absence of CD4 disruption, nearly all of the GFP+ cells were depleted, presumably due to HIV infection. As shown in FIG. 18 (right panel), in the presence of CD4 disruption, more GFP+ cells survived, likely because they were protected from HIV infection. Specifically, the percentage of GFP cells that survived HIV infection was markedly increased when CD4 was disrupted, from 0.31% to 3.11%, representing a 10-fold increase in survival. Thus, there was an increased survival of genetically modified cells during HIV infection.

Example 5—Targeting AML Cells with Anti CD4 CAR T Cells

MOLM-13 cells are an AML cell line. MOLM-13 cells were labeled by transduction with an mCherry marker. MOLM-13 cells (target cells) were incubated for 21 hours at a 1:1 ratio with either T cells containing an anti-CD4 CAR (effector cells), or control T cells not containing the anti-CD4 CAR (mock cells). Cell populations were then analyzed by flow cytometry.

Figure 19:
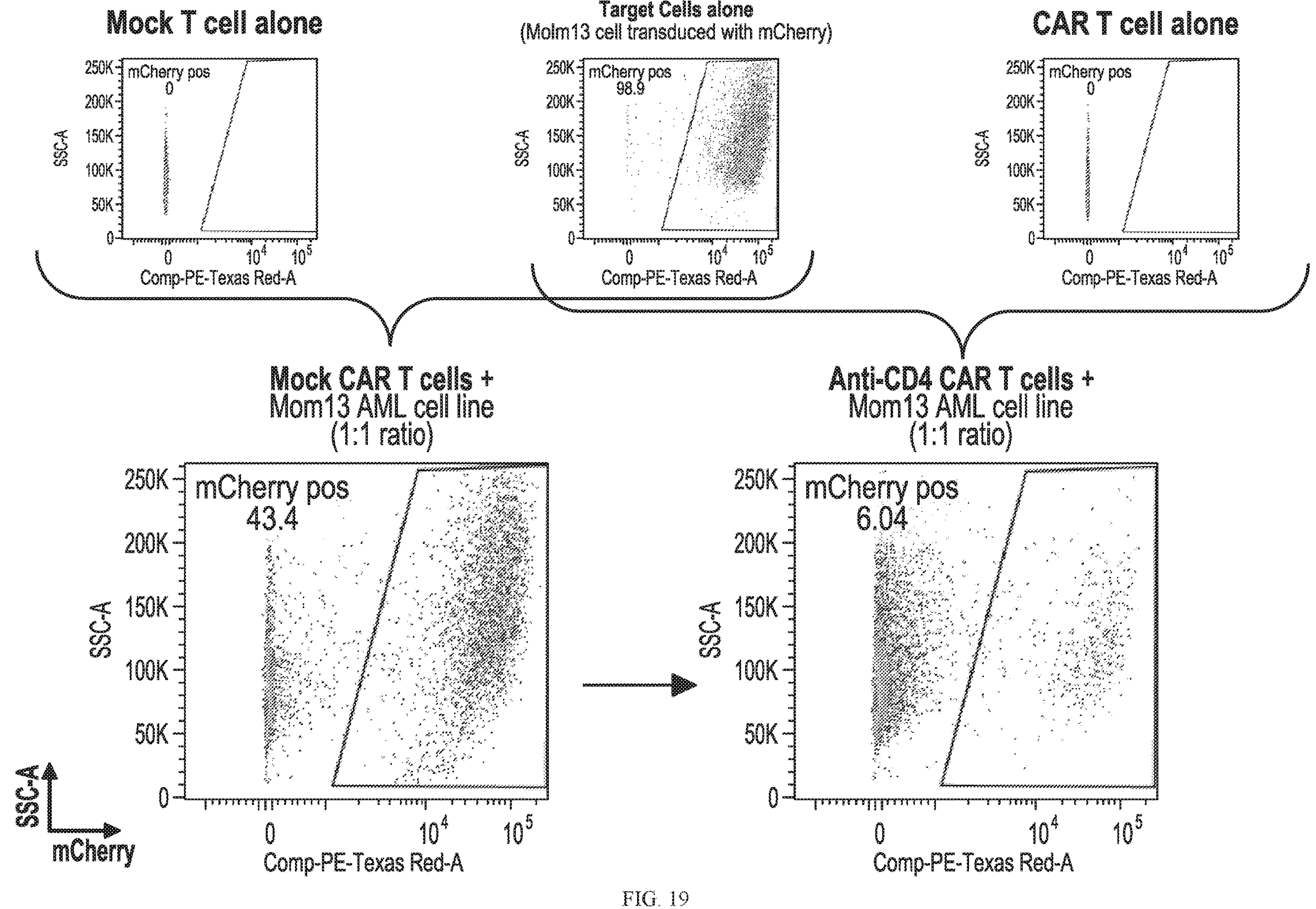
FIG. 19 depicts flow cytometry data for control T cells (mock), target AML cells (MOLM13 cells) containing an mCherry marker, and T cells containing an anti-CD4 CAR. Plots show side scatter (Y axis) versus (Texas cherry red) (X axis) generated by flow cytometry.

As shown in FIG. 19, plots show side scatter (Y axis) versus (Texas cherry red) (X axis) generated by flow cytometry. Mock T cells alone (upper left plot), AML cells alone (MOLM-13 cells) (upper center plot), and anti-CD4 CART cells alone (upper right plot). The AML (MOLM-13) target cells were transduced with mCherry. 98% of target cells were mCherry positive (upper center plot). In FIG. 19, lower plots depict results for the mock T cells or CAR T cells mixed with AML cells. The mCherry signal was reduced by 86% in the target:effector population compared to target: mock population which demonstrated that anti-CD4 CAR T cells were effective at killing the AML cells.

Example 6—Targeting AML Cells with CD4− Anti-CD4 CAR T Cells

CD4− T cells are generated as described above with Cas9 and G6 and are transduced with a polynucleotide encoding an anti-CD4 CAR. MOLM-13 cells (target cells) are labeled by transduction with an mCherry marker. MOLM-13 cells are incubated for 21 hours at a 1:1 ratio with either (1) CD4+ T cells containing an anti-CD4 CAR (effector CD4+ cells), (2) CD4− T cells containing an anti-CD4 CAR (effector CD4− cells), (3) CD4+ control T cells not containing the anti-CD4 CAR (mock CD4+ cells), or (4) CD4− control T cells not containing the anti-CD4 CAR (mock CD4− cells). Incubated cell populations are analyzed by flow cytometry. Target:effector CD4− cells demonstrate an increased level of AML cell killing compared to target: effector CD4+ cells.

The term “comprising” as used herein is synonymous with “including,” “containing,” or “characterized by,” and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and embodiments coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A genetically modified cell comprising an inactivated endogenous CD4 gene, wherein the genetically modified cell:

comprises a chimeric antigen receptor (CAR), wherein the CAR specifically binds a target antigen; and wherein the genetically modified cell is prepared by introducing into a source cell a guide RNA (gRNA), which hybridizes to a first exon or a third exon of a CD4 gene, wherein the source cell is a CD3+ cell; and wherein the genetically modified cell comprises an activity to produce a cytokine against a target cell comprising the target antigen, wherein a level of the cytokine produced by the genetically modified cell is the same or greater than a level of the cytokine produced by a cell comprising the CAR and which lacks an inactivated endogenous CD4 gene.

2. A pharmaceutical composition comprising the genetically modified cell of claim 1, and a pharmaceutically acceptable excipient.

3. A method of killing or inhibiting a population of CD4+ cells, comprising contacting the population of CD4+ cells with the genetically modified cell of claim 1.

4. A method of reducing or inhibiting HIV replication in a population of CD4+ cells comprising an HIV-infected cell, the method comprising contacting the population of CD4+ cells with the genetically modified cell of claim 1.

5. A method of treating, inhibiting, or ameliorating a disorder in a subject, wherein the disorder is selected from an HIV infection, an acute myeloid leukemia (AML) or an acute lymphocytic leukemia (ALL), comprising administering to the subject a population of cells comprising the genetically modified cell of claim 1.

6. The genetically modified cell of claim 1, wherein the source cell is a CD4+ T cell.

7. The genetically modified cell of claim 1, wherein the target antigen is CD4, CD19, or an HIV protein.

8. The genetically modified cell of claim 1, wherein the target antigen is CD4.

9. The genetically modified cell of claim 1, wherein the genetically modified cell comprises a cytotoxic activity against a target cell comprising the target antigen.

10. The genetically modified cell of claim 1, wherein the cytokine is selected from TNF-alpha, IL-2 or IFN gamma.

11. The genetically modified cell of claim 1, wherein the source cell is a CD4+ T cell and the target antigen is CD4.

12. A system comprising:

the genetically modified cell of claim 1; and a target cell comprising the target antigen.

13. The system of claim 12, wherein the target cell is selected from an HIV-infected cell, an acute myeloid leukemia (AML) cell, or an acute lymphocytic leukemia (ALL) cell.

14. A CD3+ cell comprising an inactivated endogenous CD4 gene, the cell comprising:

a guide RNA (gRNA), which hybridizes to a first exon or a third exon of a CD4 gene, a Cas 9 nuclease or polynucleotide encoding the Cas 9 nuclease, and a polynucleotide encoding a chimeric antigen receptor (CAR), wherein the CAR specifically binds a target antigen; and wherein the cell comprises an activity to produce a cytokine against a target cell comprising the target antigen, wherein a level of the cytokine produced by the cell is the same or greater than a level of the cytokine produced by a cell comprising the CAR and which lacks an inactivated endogenous CD4 gene.

15. The cell of claim 14, wherein the gRNA comprises a sequence having at least 95% sequence identity with the nucleotide sequence set forth in any one of SEQ ID NOS: 01-08 or complement thereof.

16. The cell of claim 14, wherein the gRNA comprises the sequence set forth in SEQ ID NO:06 or a complement thereof.

17. The cell of claim 14, wherein the cell is derived from a CD4+ T cell.

18. The cell of claim 14, wherein the target antigen is CD4, CD19, or an HIV protein.

19. The cell of claim 14, wherein the target antigen is CD4.

20. The cell of claim 14, wherein the gRNA comprises the sequence set forth in SEQ ID NO:08 or a complement thereof.

* * * * *